United States Patent
Shinji et al.

(10) Patent No.: US 10,972,675 B2
(45) Date of Patent: Apr. 6, 2021

(54) ENDOSCOPE SYSTEM

(71) Applicant: OLYMPUS CORPORATION, Tokyo (JP)

(72) Inventors: Sho Shinji, Tokyo (JP); Koji Matsumoto, Tokyo (JP); Tetsuhiro Oka, Tokyo (JP); Kenji Urushibata, Tokyo (JP); Hiroyuki Kubo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/691,865

(22) Filed: Nov. 22, 2019

(65) Prior Publication Data
US 2020/0099844 A1     Mar. 26, 2020

Related U.S. Application Data

(63) Continuation of application No. PCT/JP2017/021661, filed on Jun. 12, 2017.

(51) Int. Cl.
*A61B 1/04*     (2006.01)
*H04N 5/235*    (2006.01)
(Continued)

(52) U.S. Cl.
CPC ......... *H04N 5/2354* (2013.01); *A61B 1/0005* (2013.01); *A61B 1/045* (2013.01); *A61B 1/0638* (2013.01)

(58) Field of Classification Search
CPC ... A61B 1/00009; A61B 1/045; A61B 1/0638; A61B 1/00096; A61B 1/05; A61B 1/07;
(Continued)

(56) References Cited

U.S. PATENT DOCUMENTS 6,464,633 B1 * 10/2002 Hosoda ............... A61B 1/0638
                                                    348/68
7,519,096 B2    4/2009 Bouma et al.
(Continued)

FOREIGN PATENT DOCUMENTS

EP      2229870 A1     9/2010
EP      2520214 A1    11/2012
(Continued)

OTHER PUBLICATIONS

International Search Report dated Aug. 22, 2017 issued in PCT/JP2017/021661.
(Continued)

*Primary Examiner* — Gims S Philippe
(74) *Attorney, Agent, or Firm* — Scully, Scott, Murphy & Presser, P.C.

(57) ABSTRACT

An endoscope system according to the present invention includes: an illumination unit that radiates illumination light onto a subject, the illumination light having a spatially non-uniform intensity distribution including a light section and a dark section in a beam cross section orthogonal to an optical axis; an imaging unit that images an illumination image of the subject irradiated with the illumination light; and a separation processor that generates two separate images from the illumination image. Among intensity values of pixels within the illumination image respectively corresponding to the light section, the dark section, and a section having intermediate intensity between the light section and the dark section, the separation processor generates the two separate images based on at least two of the intensity values.

16 Claims, 28 Drawing Sheets

(51) Int. Cl.
*A61B 1/00* (2006.01)
*A61B 1/045* (2006.01)
*A61B 1/06* (2006.01)

(58) Field of Classification Search
CPC .... A61B 1/00; A61B 1/00045; H04N 5/2354; H04N 5/2256; G01B 11/2513
USPC .......................................................... 348/68
See application file for complete search history.

(56) References Cited

U.S. PATENT DOCUMENTS

| | | | |
|---|---|---|---|
| 2001/0055462 | A1 | 12/2001 | Seibel |
| 2002/0165456 | A1 | 11/2002 | Canpolat et al. |
| 2010/0048995 | A1 | 2/2010 | Suijver et al. |
| 2010/0056928 | A1 | 3/2010 | Zuzak et al. |
| 2010/0195078 | A1* | 8/2010 | Horiuchi ............ G03F 7/70466 355/71 |
| 2010/0240953 | A1 | 9/2010 | Murakami |
| 2010/0245551 | A1 | 9/2010 | Morita |
| 2011/0263955 | A1 | 10/2011 | Narita et al. |
| 2012/0123205 | A1 | 5/2012 | Nie et al. |
| 2012/0302847 | A1 | 11/2012 | Ozawa et al. |
| 2012/0327205 | A1 | 12/2012 | Takahashi |
| 2013/0270421 | A1* | 10/2013 | Kanamori .................. G01J 4/04 250/208.1 |
| 2014/0052005 | A1* | 2/2014 | Yokota .................. A61B 5/1076 600/477 |
| 2014/0092227 | A1* | 4/2014 | Kanamori ............. G01J 1/0209 348/68 |
| 2014/0267657 | A1* | 9/2014 | Takei ..................... A61B 1/043 348/68 |
| 2015/0022647 | A1 | 1/2015 | Takei et al. |
| 2015/0238089 | A1 | 8/2015 | Fujinuma et al. |
| 2015/0320296 | A1 | 11/2015 | Morita |
| 2016/0041334 | A1 | 2/2016 | Suijver et al. |
| 2016/0278678 | A1 | 9/2016 | Valdes et al. |
| 2017/0006202 | A1* | 1/2017 | Otani ..................... H05B 41/38 |
| 2017/0098301 | A1* | 4/2017 | Ikemoto ................ G06T 7/0012 |
| 2017/0231480 | A1 | 8/2017 | Yamazaki |
| 2018/0164221 | A1 | 6/2018 | Singh et al. |
| 2020/0099845 | A1 | 3/2020 | Matsumoto et al. |

FOREIGN PATENT DOCUMENTS

| | | |
|---|---|---|
| EP | 2526854 A1 | 11/2012 |
| EP | 2979607 A1 | 2/2016 |
| EP | 3075301 A1 | 10/2016 |
| EP | 3202306 A1 | 8/2017 |
| JP | 2009-536066 A | 10/2009 |
| JP | 2010-213992 A | 9/2010 |
| JP | 2010-227256 A | 10/2010 |
| JP | 2012-239816 A | 12/2012 |
| JP | 2014-18439 A | 2/2014 |
| JP | 2014-188222 A | 10/2014 |
| JP | 2015-077415 A | 4/2015 |
| JP | 2015-231498 A | 12/2015 |
| JP | 2016-49370 A | 4/2016 |
| JP | 2016-174836 A | 10/2016 |
| JP | 2016-198304 A | 12/2016 |
| JP | 2016-200418 A | 12/2016 |
| JP | 2016-209466 A | 12/2016 |
| JP | 2017-042629 A | 3/2017 |
| WO | WO 2007/132378 A2 | 11/2007 |
| WO | WO 2011/080996 A1 | 7/2011 |
| WO | WO 2011/081141 A1 | 7/2011 |
| WO | WO 2015/016013 A1 | 2/2015 |
| WO | WO 2016/151903 A1 | 9/2016 |
| WO | WO 2016/181720 A1 | 11/2016 |
| WO | WO 2018/229832 A1 | 12/2018 |
| WO | WO 2018/229833 A1 | 12/2018 |
| WO | WO 2018/229834 A1 | 12/2018 |

OTHER PUBLICATIONS

International Search Report dated Aug. 15, 2017 issued in PCT/JP2017/021664.
International Search Report dated Aug. 22, 2017 issued in PCT/JP2017/021665.
International Search Report dated Aug. 22, 2017 issued in PCT/JP2017/021667.
Shree K. Nayar et al., "Fast separation of direct and global components of a scene using high frequency illumination", ACM Transactions on Graphics (Jul. 3, 2006), vol. 25, Issue 3, pp. 935-944.
T. Takatani et al., "Decomposition of Reflected and Scattered Lights by Multiple Weighted Measurements", 14th Symposium on Image Recognition and Understanding (MIRU2011) (Jul. 2011).
K. Tanaka et al., "Adaptive Frequency Selection under Parallel High-frequency Illumination", 16th Symposium on Image Recognition and Understanding (MIRU2013), Collection of Extended Abstract,Information Processing Society of Japan, Yoshiki Shimotsuma, SS2-33.
T. Takatani et al.,"Decomposition of Reflected and Scattered Lights by Multiple Weighted Measurements", IPSJ SIG Technical Report (CD-ROM), vol. 2011, No. 1, ROMBUNNO.CVIM-177, No. 12, ISSN 2186-2583.
Notice of Allowance dated Oct. 14, 2020 received in U.S. Appl. No. 16/691,961.
Office Action dated Dec. 3, 2020 received in U.S. Appl. No. 16/702,964.
International Search Report dated Jul. 24, 2018 issued in International Application No. PCT/JP2018/021590, with partial English translation.
International Search Report dated Jul. 24, 2018 issued in International Application No. PCT/JP2018/021597, with partial English translation.
Office Action dated Dec. 11, 2020 received in U.S. Appl. No. 16/691,961.

* cited by examiner

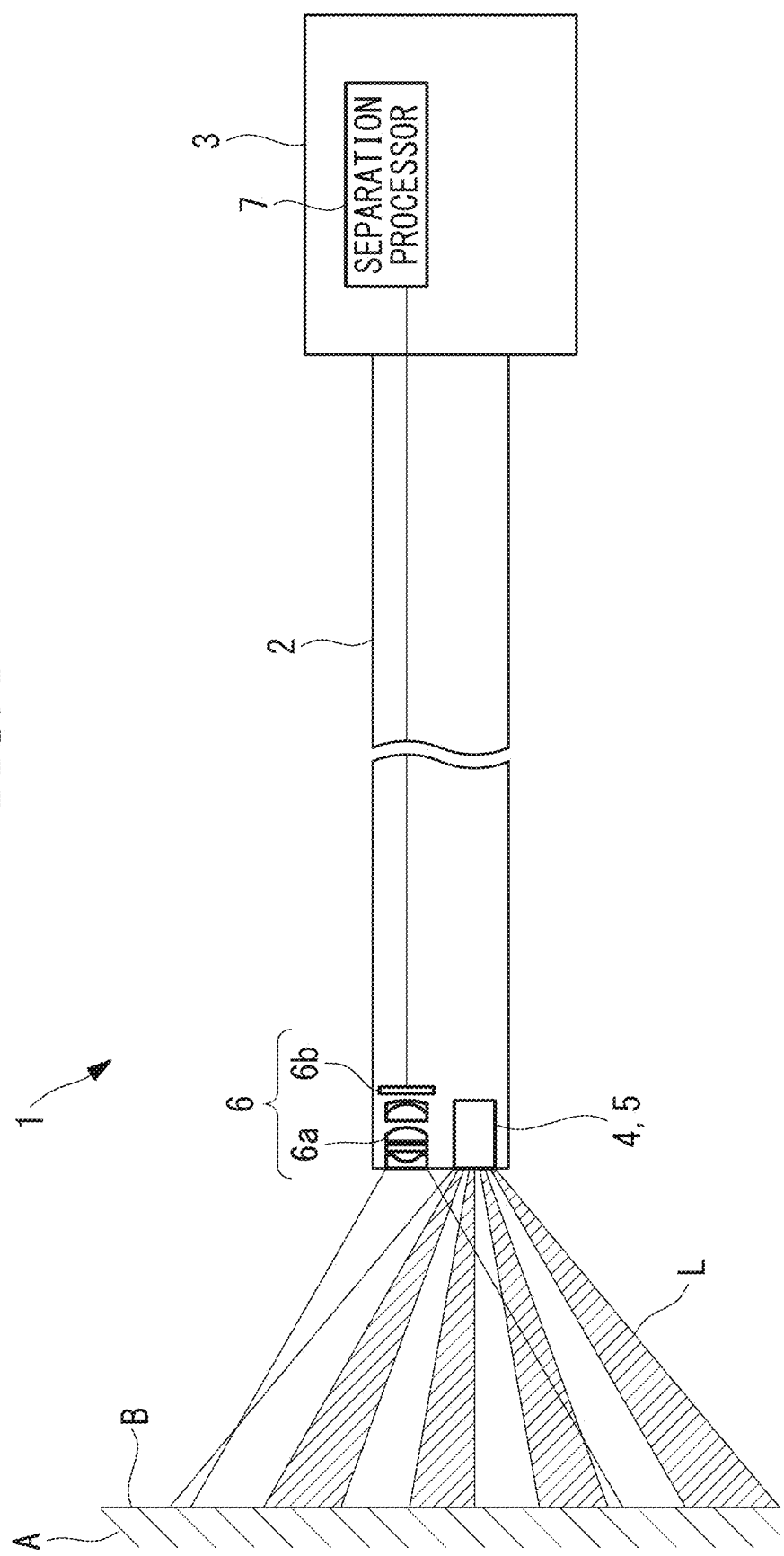

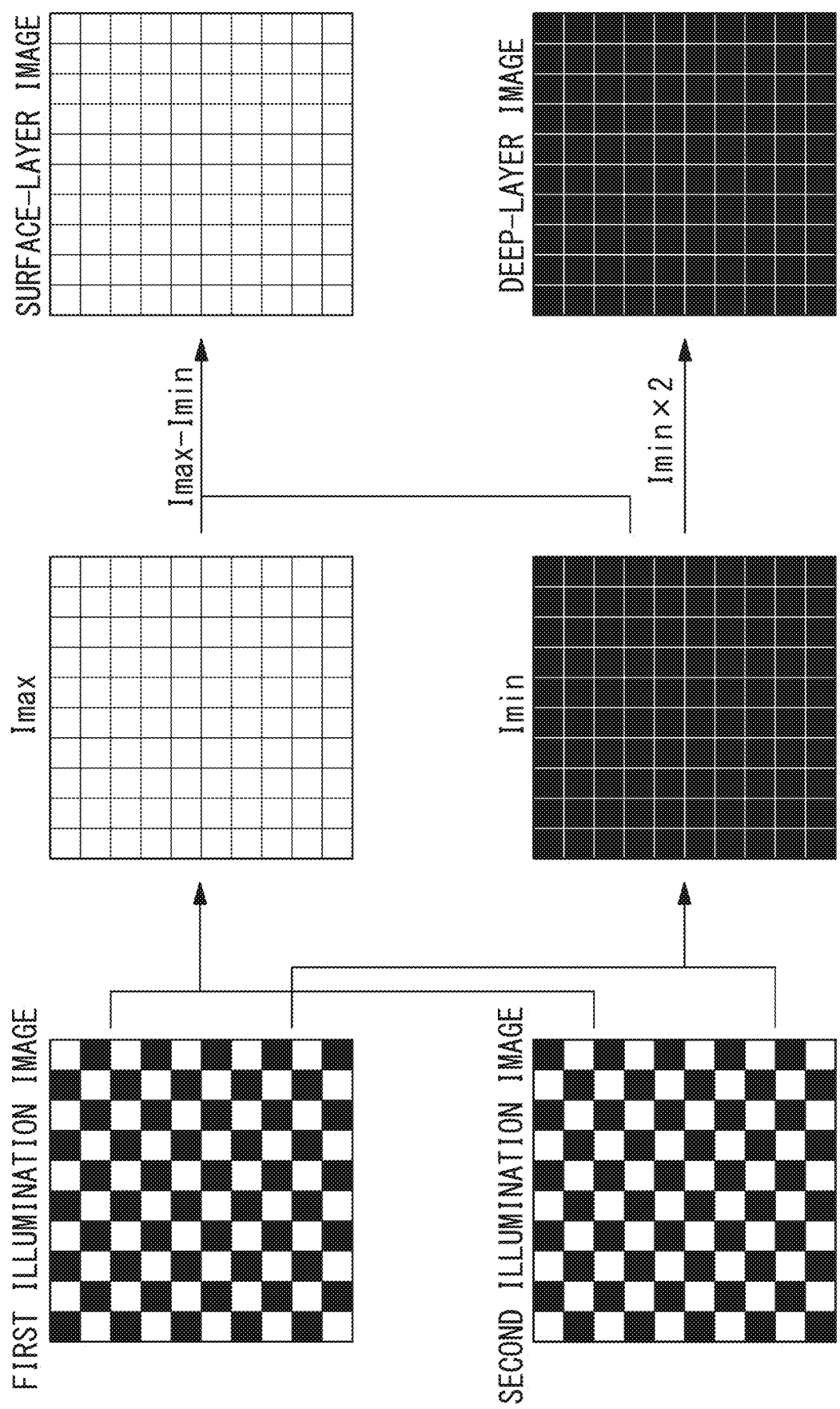

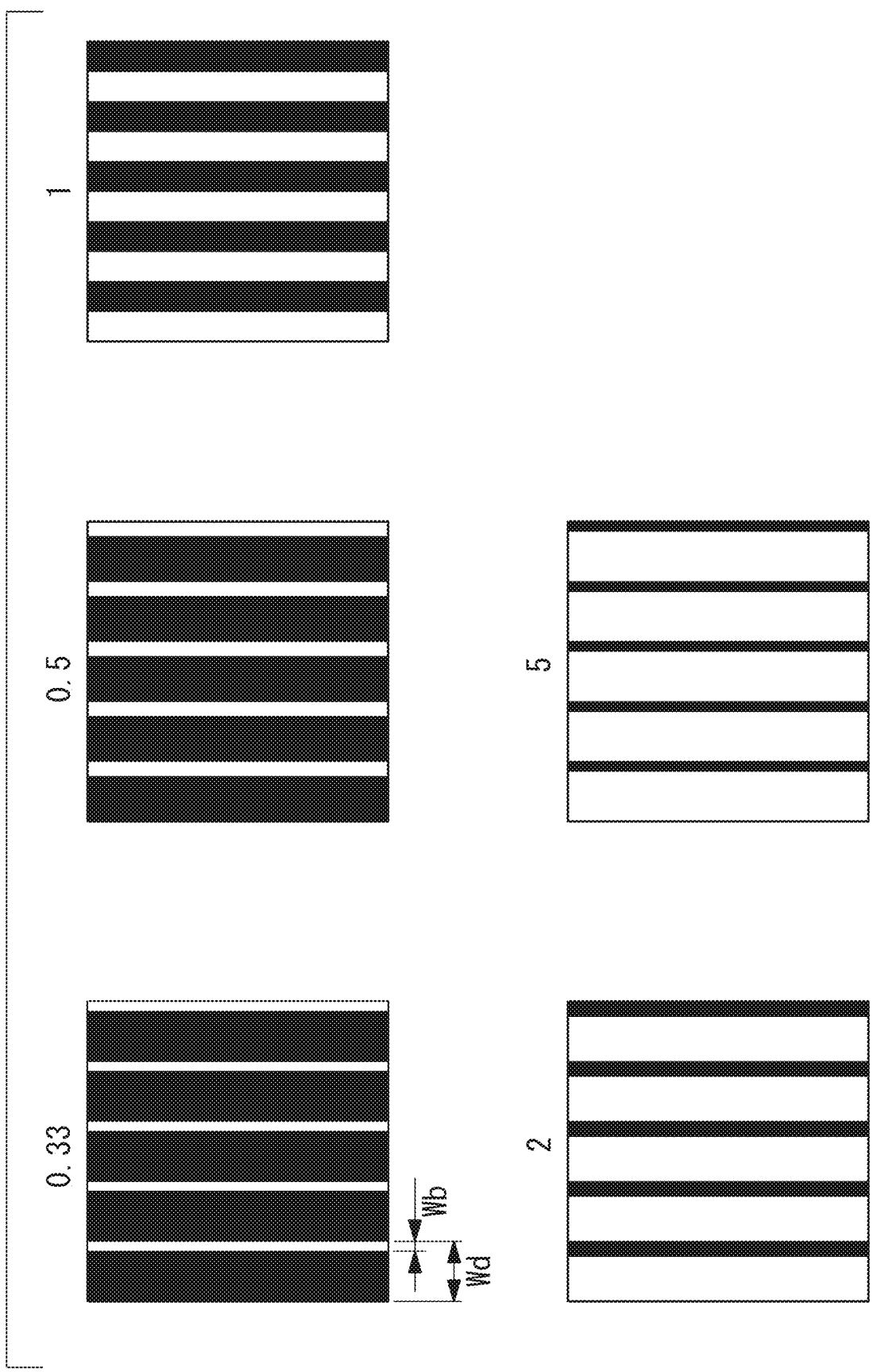

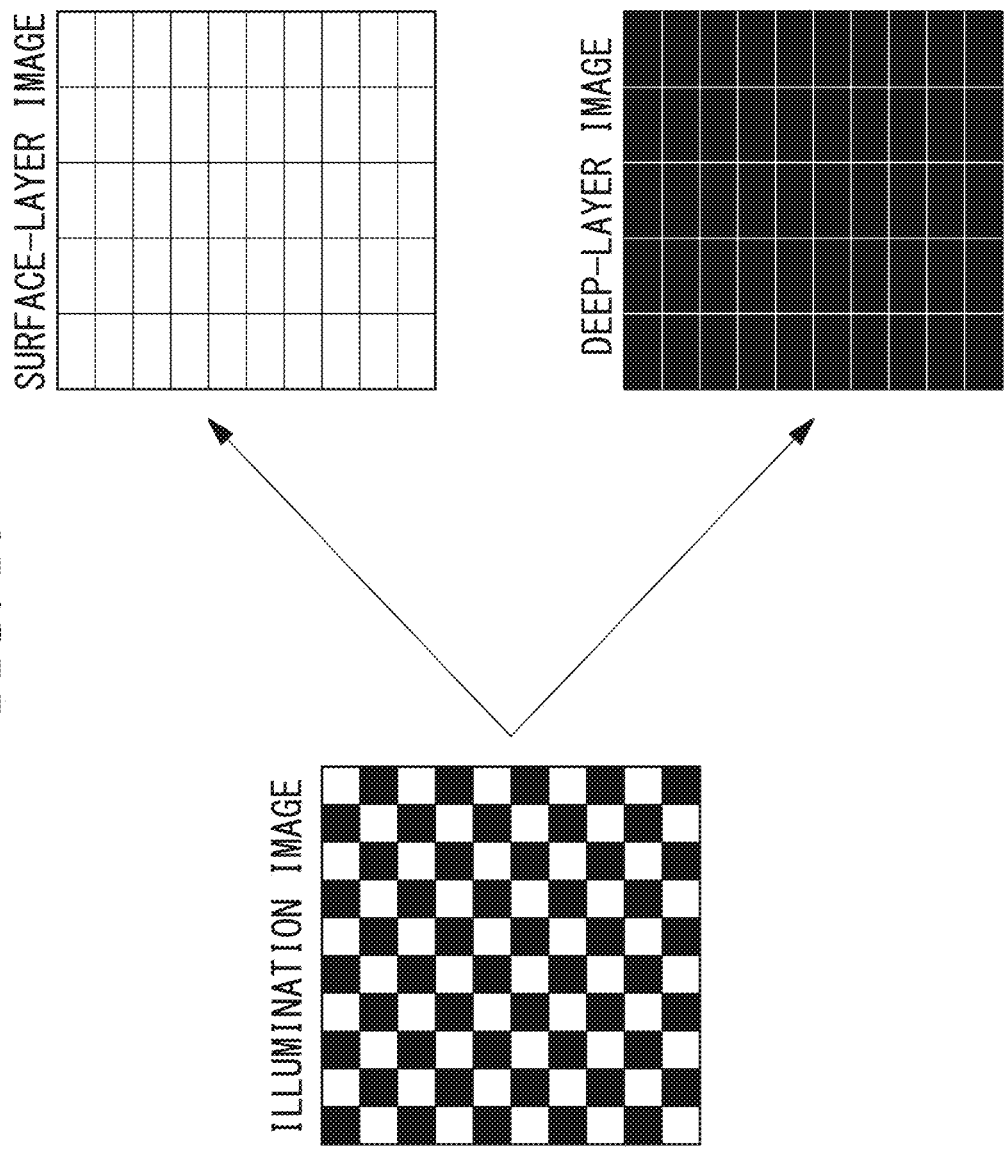

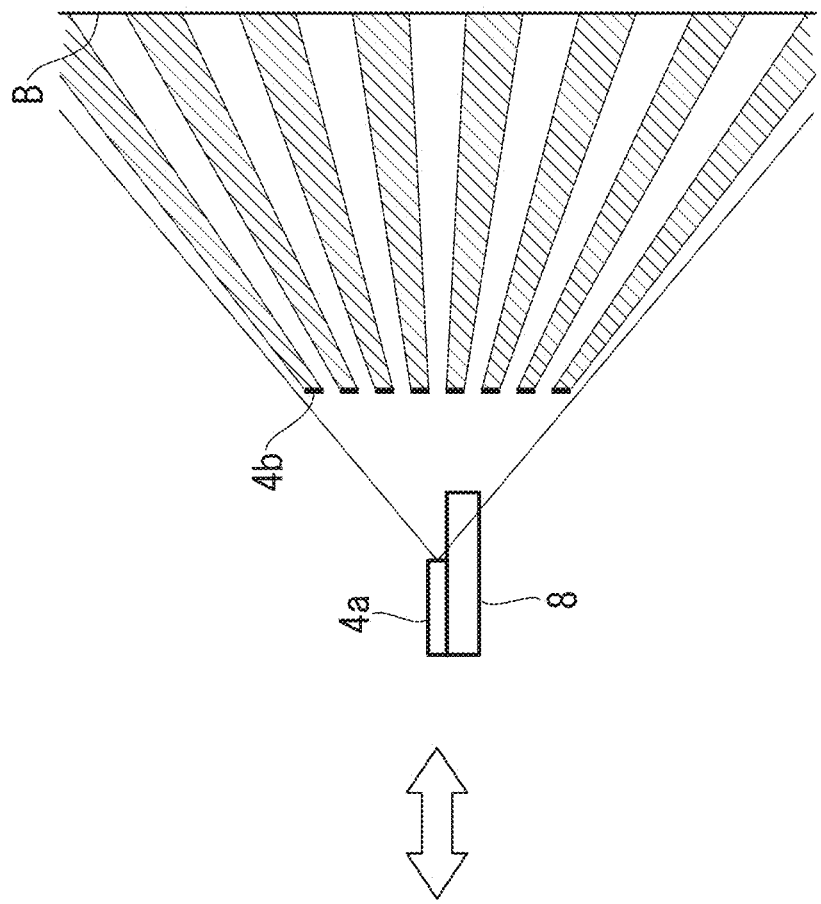
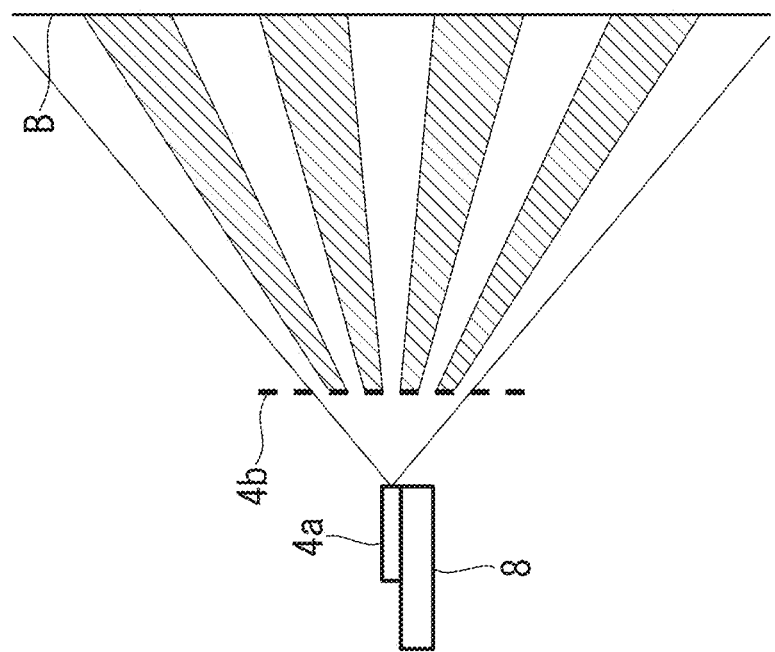
FIG. 16

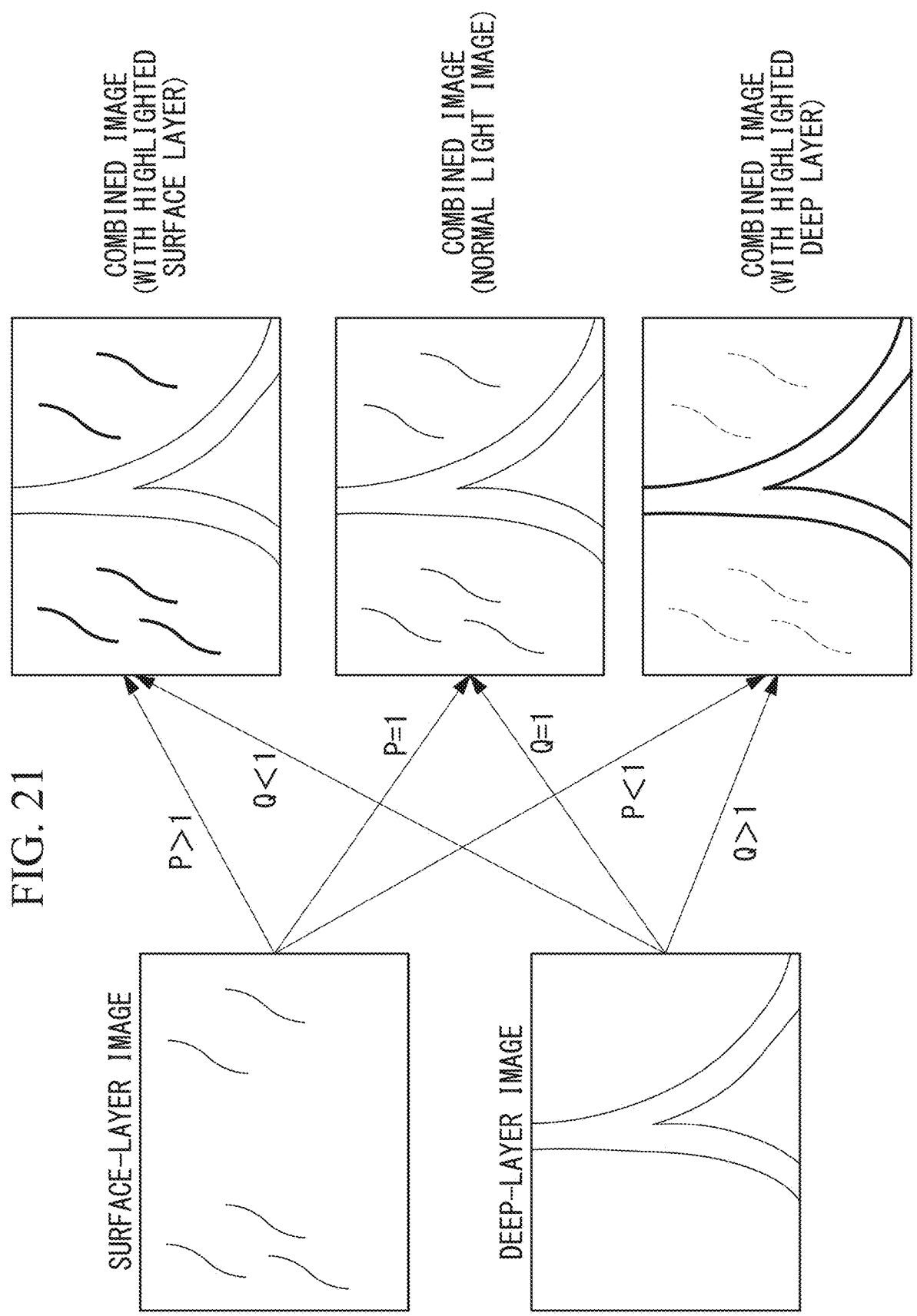

ENDOSCOPE SYSTEM

CROSS-REFERENCE TO RELATED APPLICATIONS

This is a continuation of International Application PCT/JP2017/021661, with an international filing date of Jun. 12, 2017, which is hereby incorporated by reference herein in its entirety.

TECHNICAL FIELD

The present invention relates to endoscope systems.

BACKGROUND ART

When biological tissue inside the body is to be observed through an endoscope, highlight clipping caused by specular reflection of illumination light at the mucous membrane on the surface of the biological tissue becomes a problem. There has been proposed an endoscope apparatus that can prevent such highlight clipping (e.g., see Patent Literatures 1 and 2). The apparatus according to each of Patent Literatures 1 and 2 includes an illumination polarizing plate that converts illumination light to be radiated onto a subject into linearly polarized light, and also includes an imaging polarizing plate that only allows reflected light in a polarization direction orthogonal to the polarization direction of the illumination light to enter an imaging element. The apparatus removes specularly reflected (specular) light by using the imaging polarizing plate.

CITATION LIST

Patent Literature

{PTL 1}
Japanese Unexamined Patent Application, Publication No. 2014-18439
{PTL 2}
Japanese Unexamined Patent Application, Publication No. 2016-209466

SUMMARY OF INVENTION

An aspect of the present invention provides an endoscope system including: an illumination unit that radiates illumination light onto a subject, the illumination light having a spatially non-uniform intensity distribution including a light section and a dark section in a beam cross section orthogonal to an optical axis; an imaging unit that images an illumination image of the subject irradiated with the illumination light; and a separation processor that generates two separate images from the illumination image imaged by the imaging unit. One of the two separate images is a deep-layer image including a larger amount of information about a deep-layer region of the subject than the other one of the two separate images. Among intensity values of pixels within the illumination image respectively corresponding to the light section, the dark section, and a section having intermediate intensity between the light section and the dark section in the intensity distribution, the separation processor generates the two separate images based on at least two of the intensity values.

BRIEF DESCRIPTION OF DRAWINGS

FIG. 1 illustrates the overall configuration of an endoscope system according to an embodiment of the present invention.

FIG. 5 illustrates a separate-image generating process in a separation processor.

FIG. 9 illustrates examples of light-and-dark patterns with different ratios between the area of light sections and the area of dark sections.

FIG. 10 illustrates a modification of the separate-image generating process in the separation processor.

FIG. 16 illustrates a configuration example of an intensity-distribution adjusting unit.

FIG. 21 illustrates a process performed by an image combining unit for combining a surface-layer image and a deep-layer image.

DESCRIPTION OF EMBODIMENTS

Figure 2A:
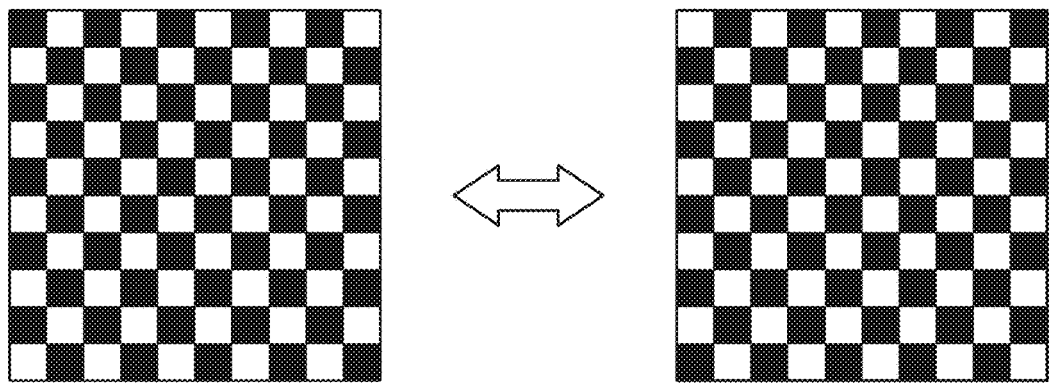
FIG. 2A illustrates an example of the intensity distribution of illumination light and a temporal change thereof.

An endoscope system 1 according to an embodiment of the present invention will be described below with reference to the drawings.

As shown in FIG. 1, the endoscope system 1 according to this embodiment includes an endoscope 2 for observing the inside of the body, and a main unit 3 connected to the base end of the endoscope 2.

The endoscope system 1 also includes an illumination unit 4 that emits illumination light L having a light-and-dark pattern from the distal end of the endoscope 2 toward biological tissue (subject) A inside the body, an intensity-distribution changing unit 5 that temporally changes the light-and-dark pattern of the illumination light L, an imaging unit 6 that images an illumination image of the biological tissue A irradiated with the illumination light L, and a separation processor 7 that generates two separate images having information at different depths within the biological tissue A from the illumination image.

The illumination unit 4 generates white illumination light L having a spatially non-uniform intensity distribution in a beam cross section that is orthogonal to the optical axis, and emits the illumination light L toward the biological tissue A. The illumination light L normally has an intensity gradient in which the brightness gradually decreases from the center of the beam toward the periphery thereof. In addition to such an overall intensity gradient in the beam cross section, the illumination light L has a light-and-dark pattern in which high-intensity light sections and dark sections that have lower intensity than the light sections are alternately repeated in the beam cross section.

The intensity-distribution changing unit 5 temporally changes the intensity distribution of the illumination light L such that the light sections and the dark sections are interchanged in the beam cross section. Accordingly, the light sections, the dark sections, and sections having intermediate intensity between the light sections and the dark sections are projected onto positions within an irradiation range of the illumination light L on a surface B of the biological tissue A.

FIGS. 2A to 2F each illustrate an example of a light-and-dark pattern of the intensity distribution of the illumination light L and a temporal change thereof. In FIGS. 2A to 2F, a white area indicates a light section, and a black area indicates a dark section.

The light-and-dark pattern in FIG. 2A is a checkered pattern in which square light and dark sections are alternately repeated in two directions orthogonal to each other.

Figure 2B:
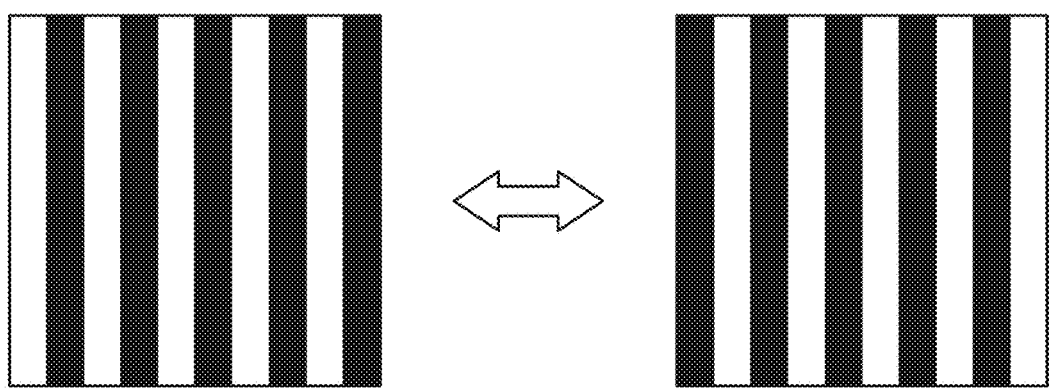
FIG. 2B illustrates another example of the intensity distribution of illumination light and a temporal change thereof.
Figure 2C:
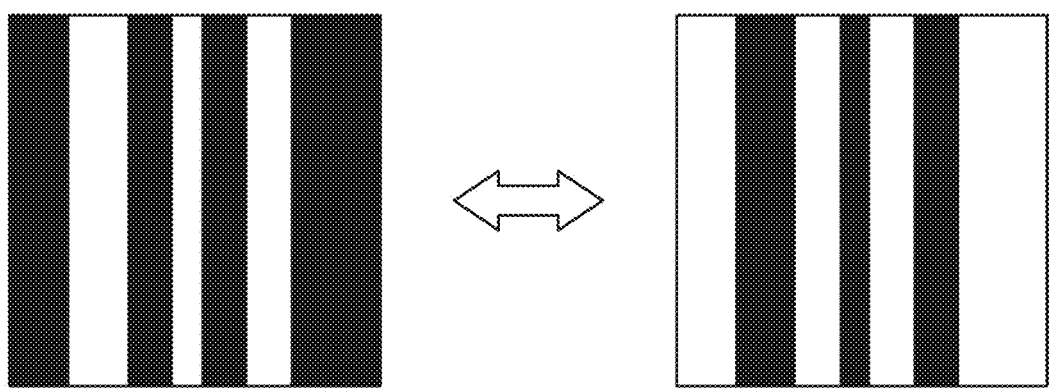
FIG. 2C illustrates another example of the intensity distribution of illumination light and a temporal change thereof.

Each of the light-and-dark patterns in FIGS. 2B and 2C is a striped pattern in which straight stripe-like light and dark sections are alternately repeated only in the width direction that is orthogonal to the longitudinal direction of the light and dark sections. In the striped pattern, the spatial period of the light and dark sections may be fixed, as shown in FIG. 2B, or may be varied, as shown in FIG. 2C.

Figure 2D:
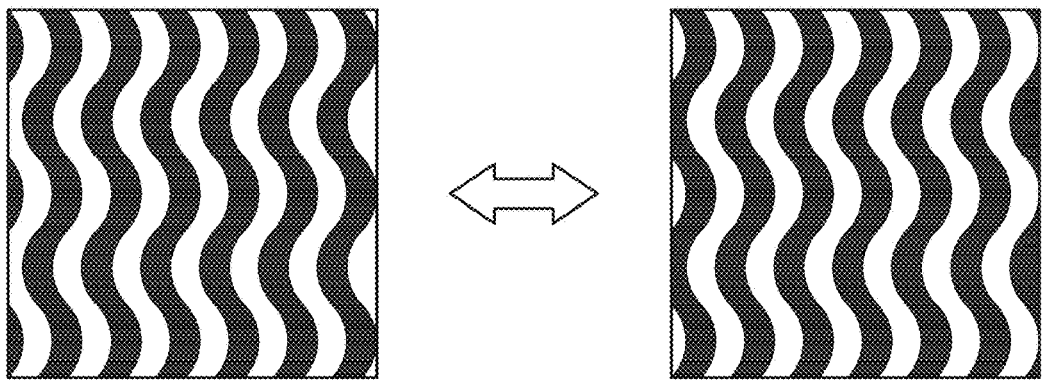
FIG. 2D illustrates another example of the intensity distribution of illumination light and a temporal change thereof.

The light-and-dark pattern in FIG. 2D is a striped pattern in which wavy stripe-like light and dark sections are alternately repeated only in the width direction that is orthogonal to the longitudinal direction of the light and dark sections.

Figure 2E:
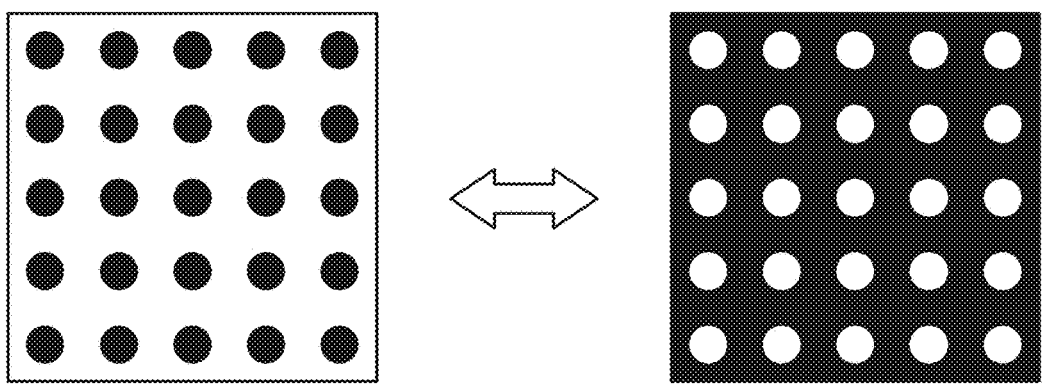
FIG. 2E illustrates another example of the intensity distribution of illumination light and a temporal change thereof.

The light-and-dark pattern in FIG. 2E is a dotted pattern in which the light sections or the dark sections are circles, whereas the other is the background.

Figure 2F:
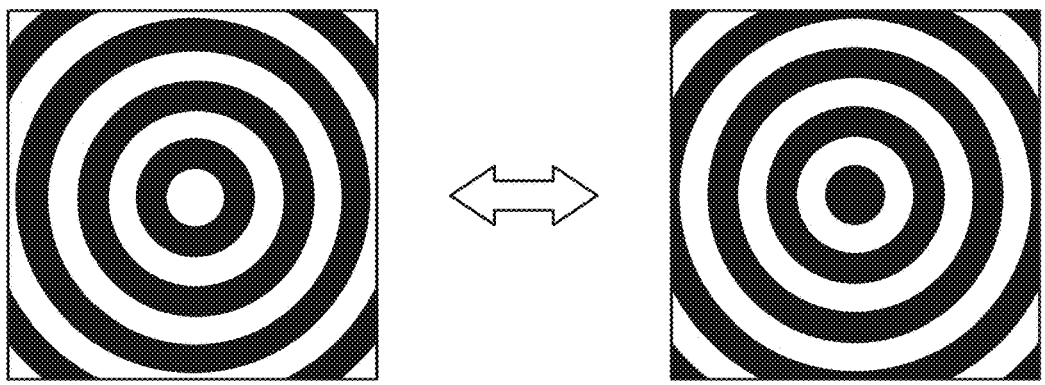
FIG. 2F illustrates another example of the intensity distribution of illumination light and a temporal change thereof.

The light-and-dark pattern in FIG. 2F is a concentric circle pattern in which circular stripe-like light sections and dark sections are alternately repeated in the radial direction.

Figure 3A:
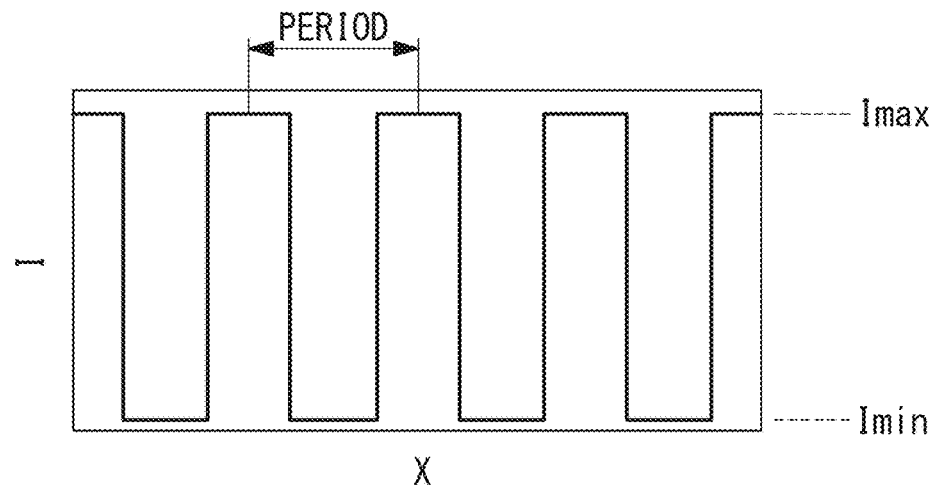
FIG. 3A illustrates an example of a spatial profile of the intensity of illumination light.
Figure 3B:
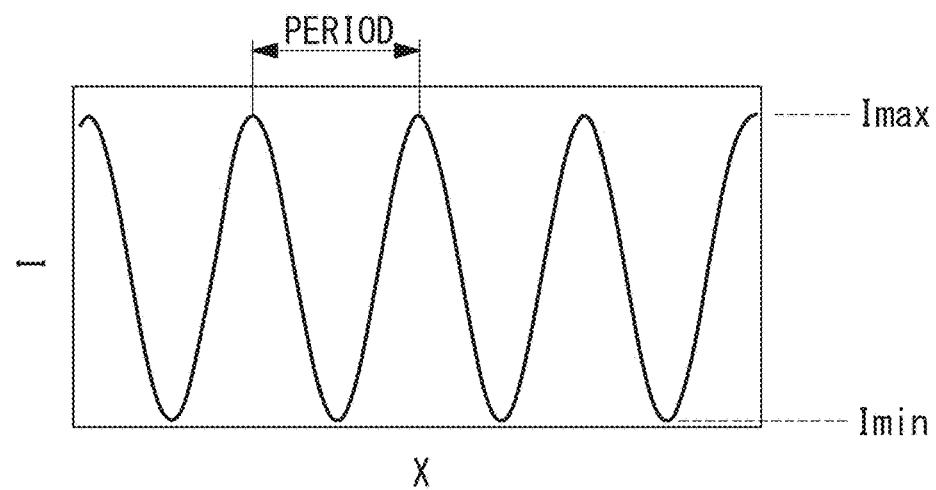
FIG. 3B illustrates another example of the spatial profile of the intensity of illumination light.
Figure 3C:
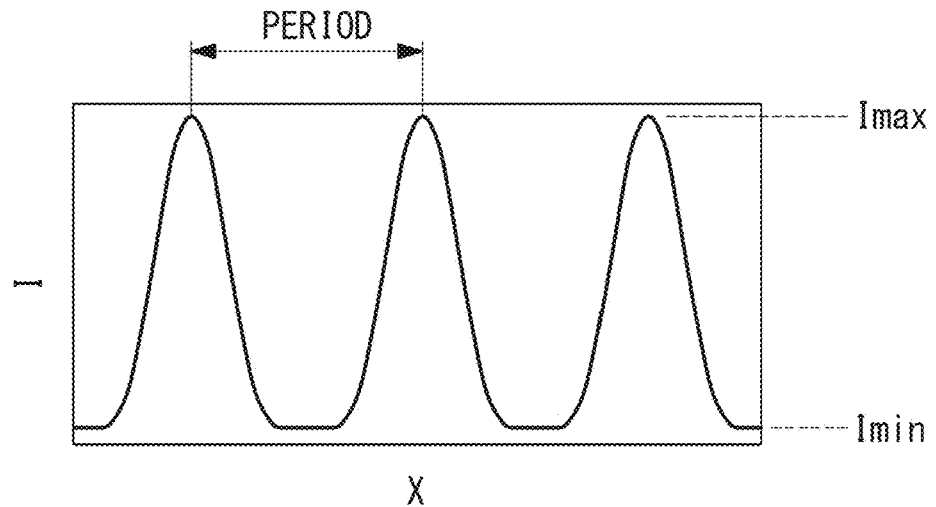
FIG. 3C illustrates another example of the spatial profile of the intensity of illumination light.
Figure 3D:
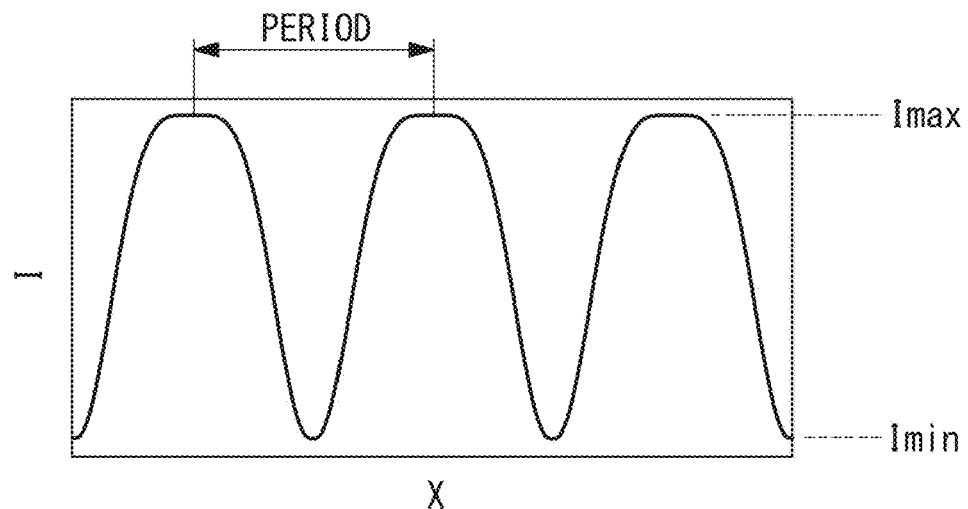
FIG. 3D illustrates another example of the spatial profile of the intensity of illumination light.
Figure 3E:
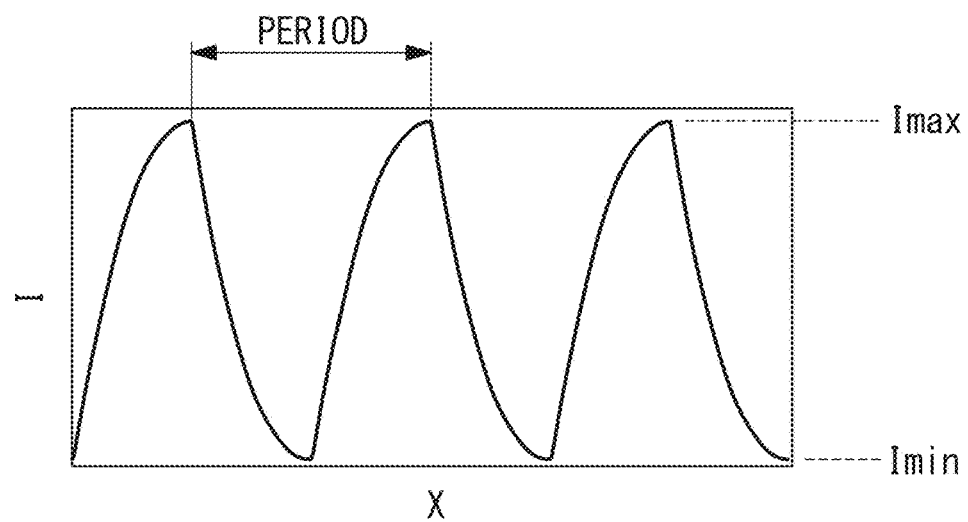
FIG. 3E illustrates another example of the spatial profile of the intensity of illumination light.
Figure 3F:
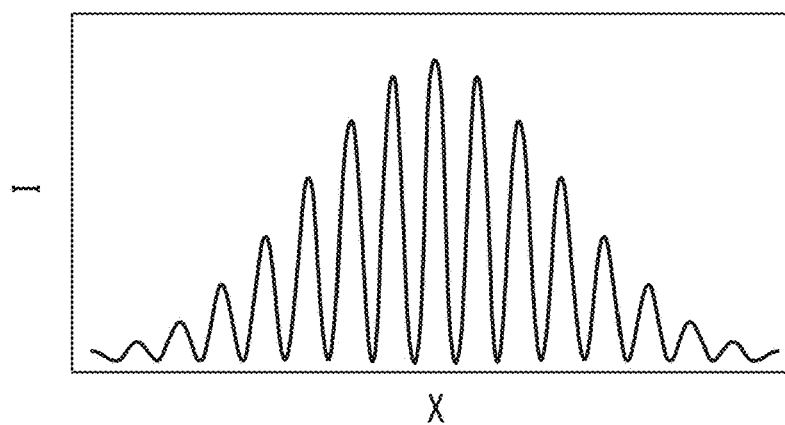
FIG. 3F illustrates another example of the spatial profile of the intensity of illumination light.

FIGS. 3A to 3F each illustrate an example of an intensity profile indicating a spatial change in intensity I between the light sections and the dark sections in each of the light-and-dark patterns in FIGS. 2A to 2F. The abscissa axis indicates a position X. The intensity profile may be a rectangular wave as shown in FIG. 3A, a sinusoidal wave as shown in FIG. 3B, an intermediate shape of a rectangular wave and a sinusoidal wave as shown in FIGS. 3C and 3D, or an asymmetrical wave as shown in FIG. 3E. As shown in FIG. 3F, the intensity profile may be the highest at the center of the illumination light L and may entirely decrease from the center toward the periphery thereof. The period of the light and dark sections may be set as the interval between each light section and a neighboring light section in each of FIGS. 3A to 3F.

FIGS. 4A to 4G each illustrate a configuration example of the illumination unit 4 and the intensity-distribution changing unit 5.

Figure 4A:
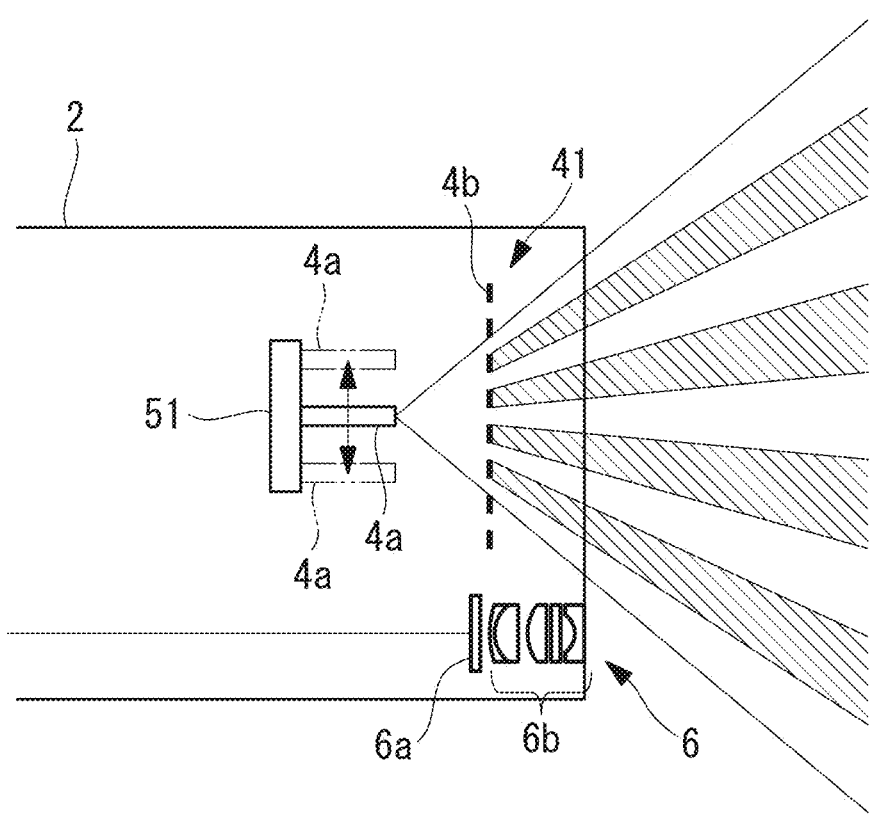
FIG. 4A illustrates a configuration example of an illumination unit and an intensity-distribution changing unit.

An illumination unit 41 in FIG. 4A forms a light-and-dark pattern on the surface B of the biological tissue A in the form of a silhouette, and includes a light emitter 4a and a mask 4b that are provided at the distal end of the endoscope 2.

Figure 4B:
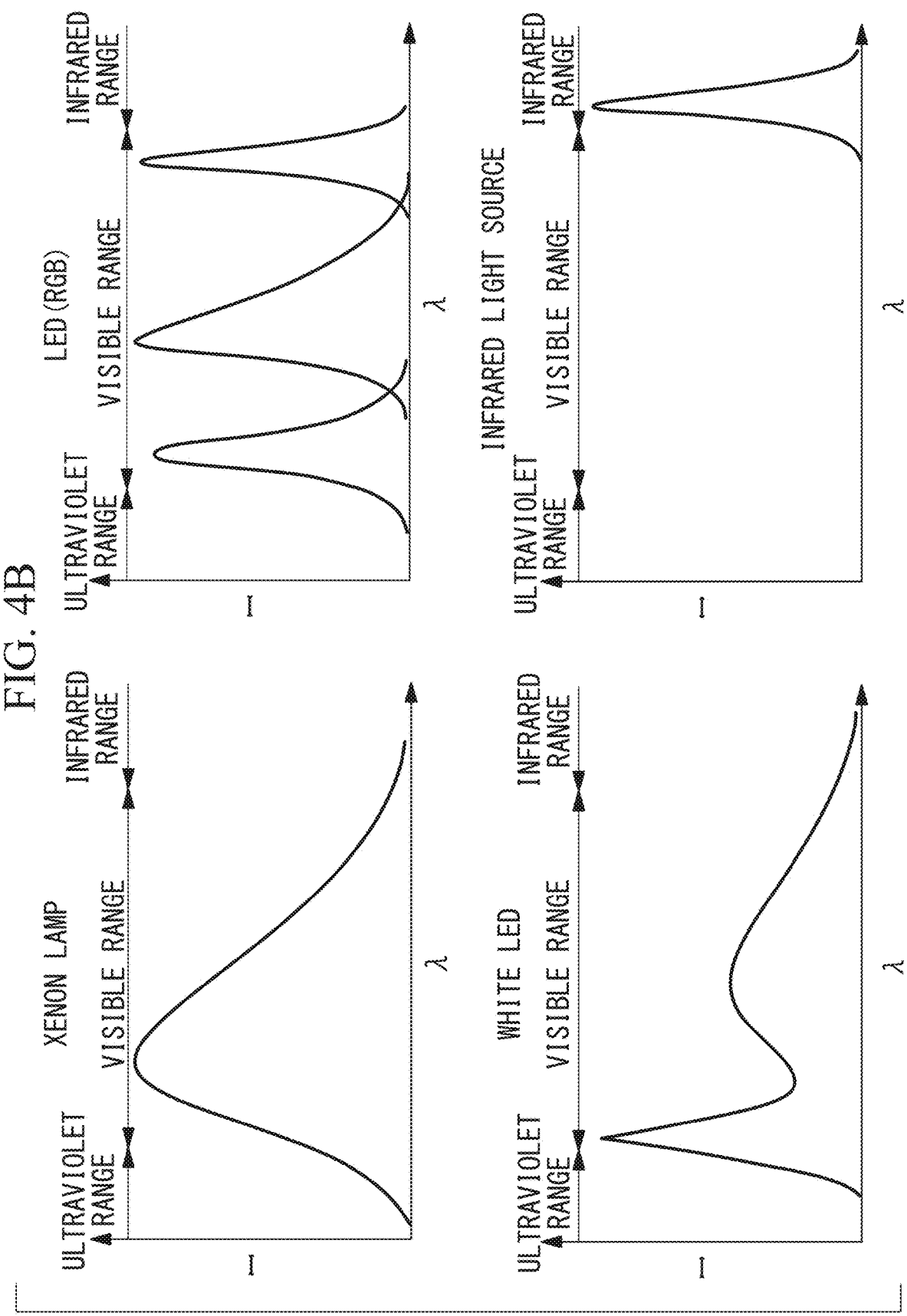
FIG. 4B illustrates an example of wavelength characteristics of a light emitter in the illumination unit in FIG. 4A.

For example, the light emitter 4a is a light source, such as a xenon lamp, an LED (RGB), a white LED, or an infrared light source, the wavelength characteristics of which are shown in FIG. 4B. In FIG. 4B, the abscissa axis indicates a wavelength λ, whereas the ordinate axis indicates the intensity I. Alternatively, the light emitter 4a may be a xenon lamp disposed outside the main unit 3, or may be an emission end of an optical fiber connected to a light source (not shown), such as a semiconductor light source including an LED or an LD.

The mask 4b has light transmission regions that allow white light to be transmitted therethrough and light blocking regions that block the white light, so that a projection pattern corresponding to the light-and-dark pattern is formed by the light transmission regions and the light blocking regions. For example, such a mask 4b is formed of a light blocking plate having openings serving as the light transmission regions or a transparent plate having a light transmission film serving as the light blocking regions. The white light emited from the light emitter 4a is transmitted through the mask 4b, so as be formed into the illumination light L having the light-and-dark pattern.

Figure 4C:
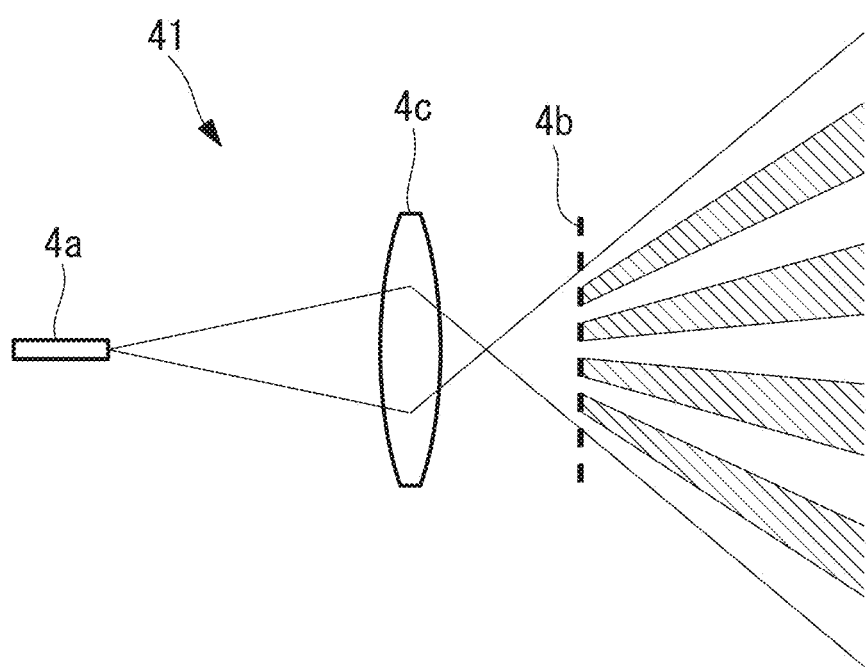
FIG. 4C illustrates another configuration example of the illumination unit and the intensity-distribution changing unit.

As shown in FIG. 4C, a lens 4c may further be provided between the light emitter 4a and the mask 4b, and the lens 4c may have a focal point between the lens 4c and the mask 4b. The divergence angle of the white light from the light emitter 4a may be changed by the lens 4c such that the illumination light L radiated onto the biological tissue A has a desired divergence angle.

An intensity-distribution changing unit 51 relatively moves the light emitter 4a and the mask 4b in a direction intersecting the optical axis of the white light, so as to temporally change the intensity distribution. Thus, the intensity-distribution changing unit 51 includes an actuator that moves at least one of the light emitter 4a and the mask 4b. As an alternative to the example in FIG. 4A in which the light emitter 4a alone is moved, the mask 4b alone may be moved, or the light emitter 4a and the mask 4b may both be moved.

The intensity-distribution changing unit 51 is suitable for the striped light-and-dark patterns in FIGS. 2B to 2D that can be temporally changed in accordance with the relative movement of the light emitter 4a and the mask 4b only in the width direction orthogonal to the longitudinal direction of the light and dark sections.

Figure 4D:
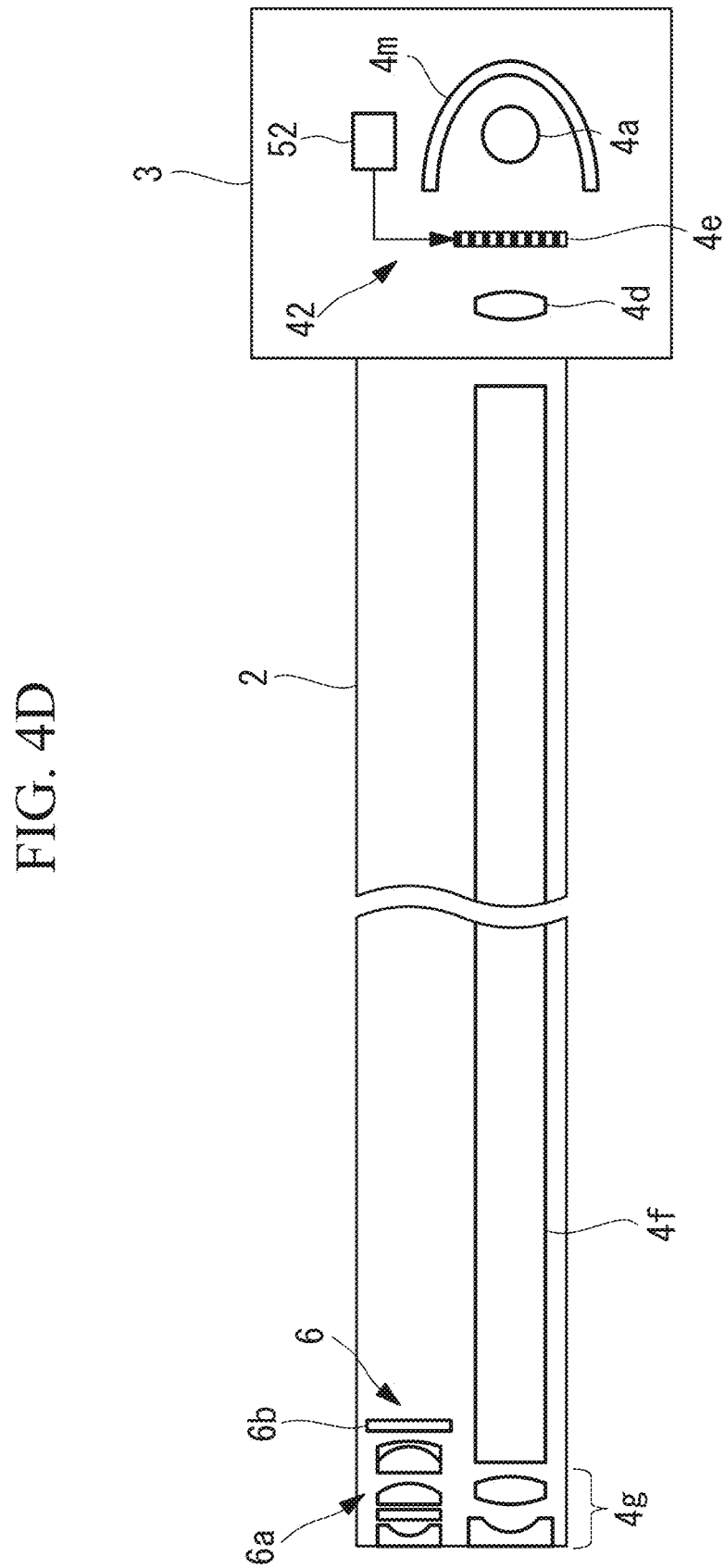
FIG. 4D illustrates another configuration example of the illumination unit and the intensity-distribution changing unit.

An illumination unit 42 in FIG. 4D includes a light emitter 4a, a focusing lens 4d, and a mask 4e that are provided in the main unit 3, and also includes an image guide fiber 4f and a projector lens 4g that are provided in the endoscope 2.

White light emitted from the light emitter 4a is collected by a reflector 4m so as to illuminate the mask 4e. The mask 4e is a liquid crystal element that can electrically control the light transmittance at each position within an input region that receives the white light, and has a light-and-dark pattern similar to that of the mask 4b. An image of the mask 4e is focused by the focusing lens 4d onto an input end surface of the image guide fiber 4f, is optically guided by the image guide fiber 4f to the projector lens 4g provided at the distal end of the endoscope 2 while the light-and-dark pattern is maintained, and is emitted from the distal end of the endoscope 2 by the projector lens 4g.

An intensity-distribution changing unit 52 includes a control element that controls the light transmittance at each position within the input region of the mask 4e.

The mask 4e formed of a liquid crystal element can form an arbitrary projection pattern and can also freely temporally change an arbitrary projection pattern, so that the illumination unit 42 is suitable for all light-and-dark patterns shown in FIGS. 2A to 2F.

Figure 4E:
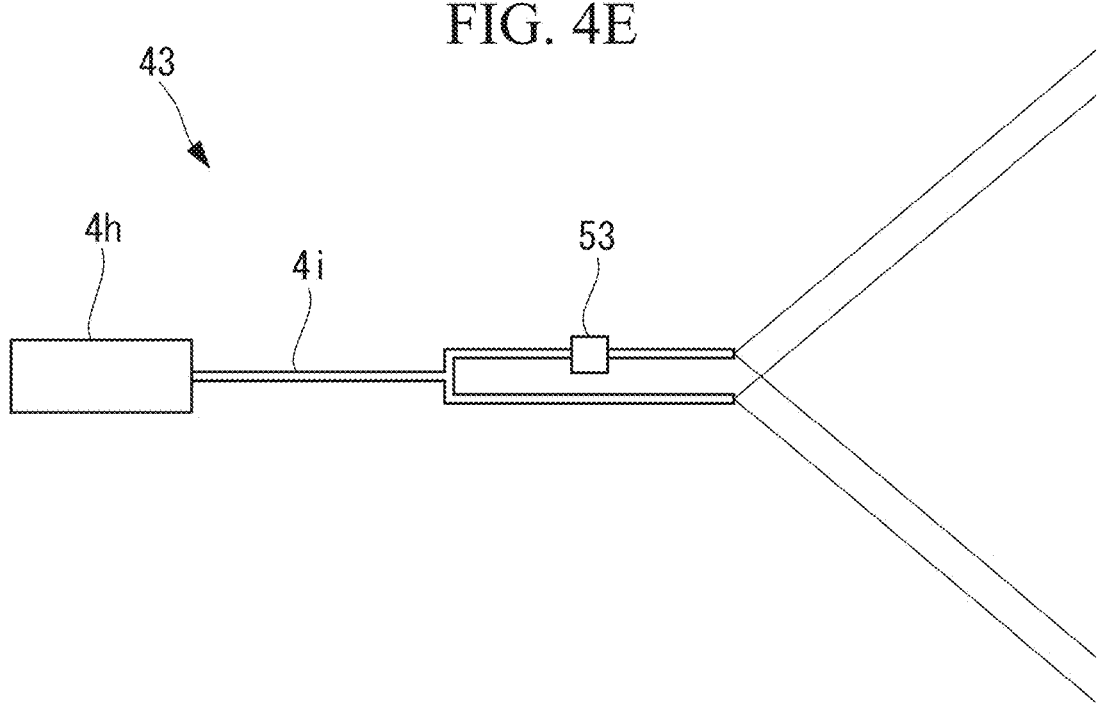
FIG. 4E illustrates another configuration example of the illumination unit and the intensity-distribution changing unit.

An illumination unit 43 in FIG. 4E uses an interference pattern of light as a light-and-dark pattern and includes a laser light source 4h and an optical path 4i that splits light emitted from the laser light source 4h into two light beams and emits the two light beams. For example, the optical path 4i is constituted by an optical fiber. The two light beams emitted from the optical path 4i interfere with each other so that an interference pattern having a sinusoidal intensity profile, as shown in FIG. 4F, is generated as a light-and-dark pattern.

Figure 4F:
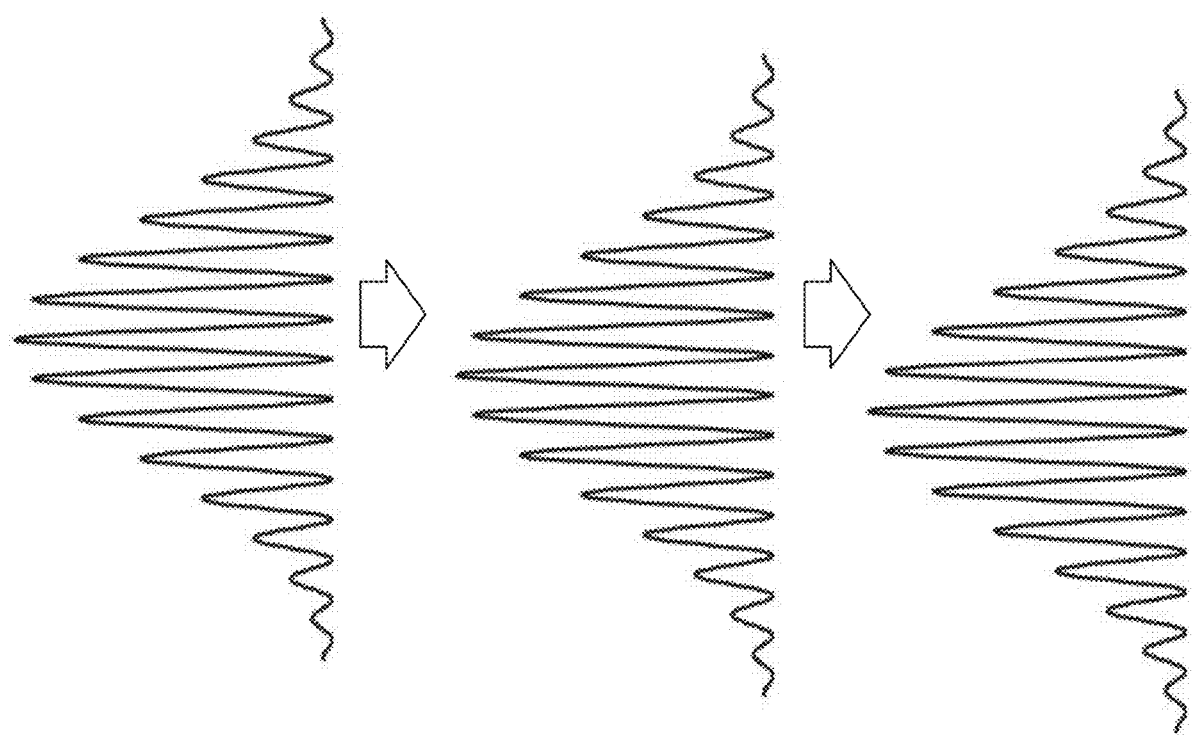
FIG. 4F illustrates a light-and-dark pattern of illumination light generated by the illumination unit in FIG. 4E and a temporal change thereof.

An intensity-distribution changing unit 53 changes the optical length of one of the two split light beams so as to shift the position of the interference pattern in a direction orthogonal to the optical axis of the illumination light, as shown in FIG. 4F. Thus, the intensity-distribution changing unit 53 includes an optical element that is provided in the optical path of one of the two light beams and that changes the optical length.

Figure 4G:
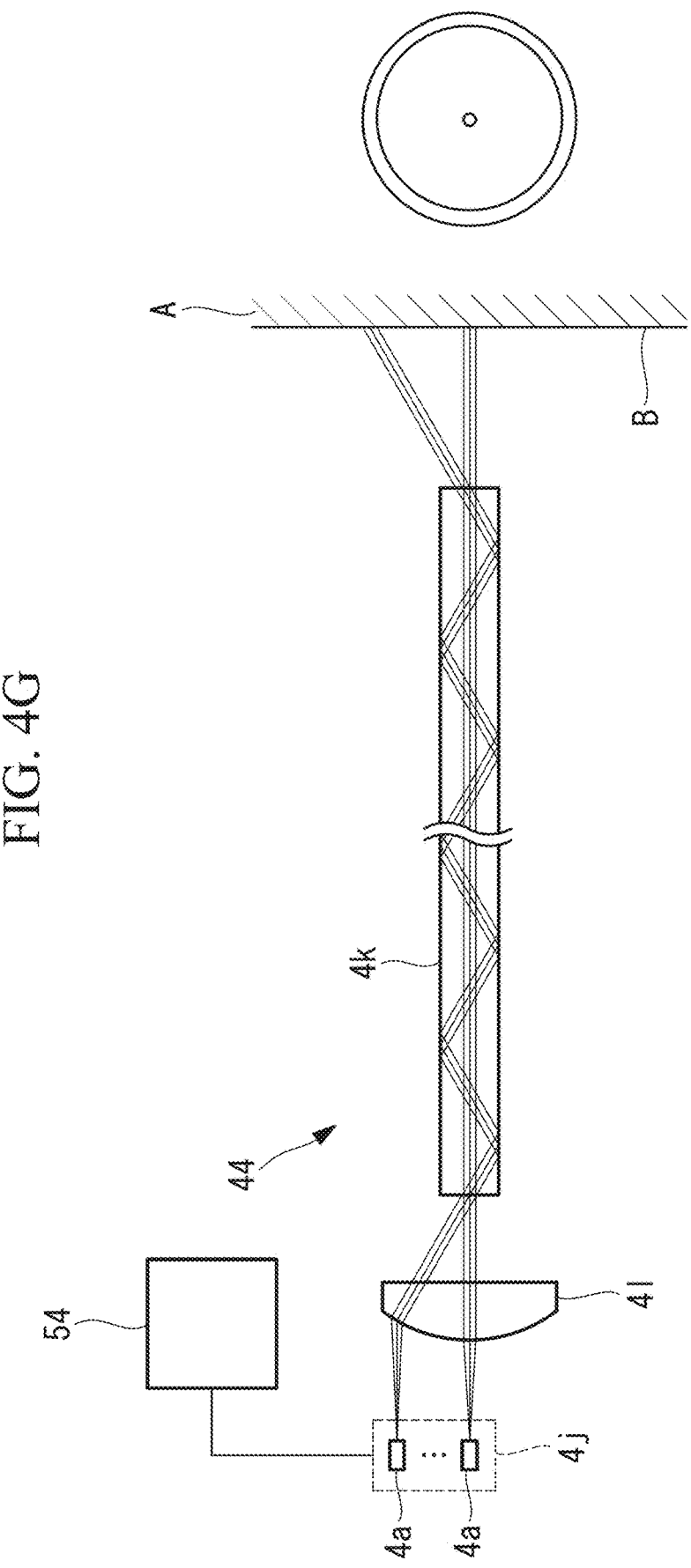
FIG. 4G illustrates another configuration example of the illumination unit and the intensity-distribution changing unit.

An illumination unit 44 in FIG. 4G includes a light source array 4j and a light guide member 4k that optically guides light while maintaining the incidence angle of the light relative to the optical axis. The light source array 4j has a plurality of light emitters 4a arranged such that light beams enter the input end of the light guide member 4k at different incidence angles from one another. Although the plurality of light emitters 4a are arranged in a single line in FIG. 4G, the plurality of light emitters 4a may be arranged two-dimensionally. The light guide member 4k is, for example, a rod lens or a multi-mode fiber.

The light emitted from each light emitter 4a is converted into a collimated light beam by a lens 41 and enters the input end of the light guide member 4k. The light entering the light guide member 4k is optically guided through the light guide member 4k while the angle thereof is maintained, and is emitted toward the biological tissue A from the emission end of the light guide member 4k at the same angle as the incidence angle to the input end. Because the light expands in the circumferential direction by repeating reflection within the light guide member 4k, the light emitted from the light guide member 4k is ring-shaped. Therefore, by turning on the plurality of light emitters 4a simultaneously, illumination light L having the concentric pattern shown in FIG. 2F is generated.

An intensity-distribution changing unit 54 performs on-and-off control of each light emitter 4a and changes the intensity distribution by switching between light emitters 4a to be turned on. Thus, the intensity-distribution changing unit 54 includes a control element that performs on and off control of each light emitter 4a.

Figure 6:
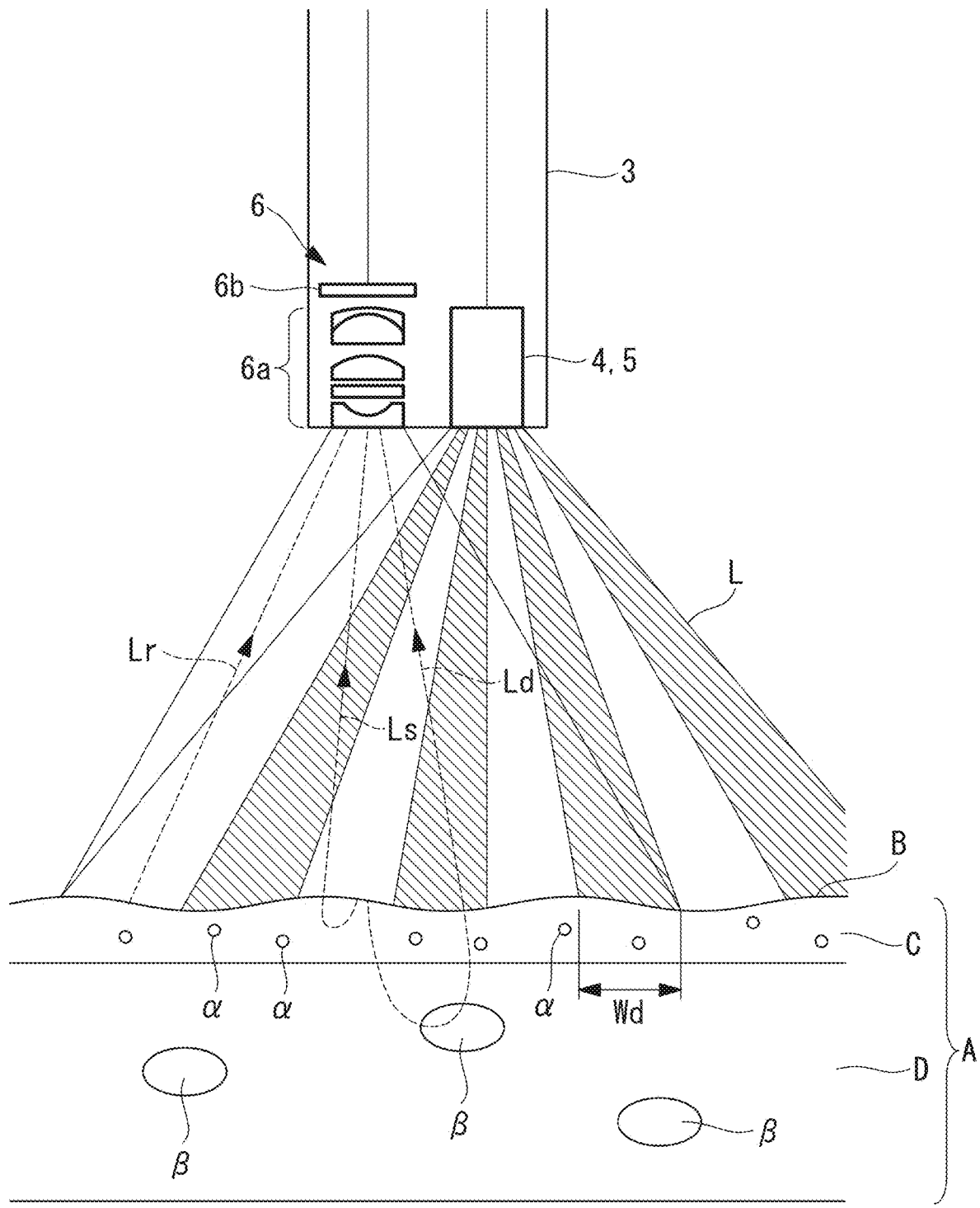
FIG. 6 illustrates the relationship between specular light, surface-scattered light, and internally scattered light that occur in biological tissue as a result of the biological tissue being irradiated with illumination light and the positions of occurrences of the specular light, the surface-scattered light, and the internally scattered light.

FIG. 6 illustrates the relationship between specular light Lr, surface-scattered light Ls, and internally scattered light Ld that occur in the biological tissue A as a result of the biological tissue A being irradiated with the illumination light L and the positions of occurrences of the specular light Lr, the surface-scattered light Ls, and the internally scattered light Ld.

The imaging unit 6 includes an imaging lens 6a that is provided at the distal end of the endoscope 2 and that collects light from the biological tissue A, and also includes an imaging element 6b that images an image of the biological tissue A formed by the imaging lens 6a. The illumination image imaged by the imaging element 6b is transmitted to the separation processor 7 from the imaging element 6b.

The intensity distribution of the illumination light L radiated onto the biological tissue A is temporally changed by the intensity-distribution changing unit 5, as shown in FIGS. 2A to 2F. The imaging element 6b performs an imaging process at two time points by radiating illumination light L, in which the light sections and the dark sections are inverted, onto the biological tissue A, thereby imaging two illumination images (i.e., a first illumination image and a second illumination image) in which the projection regions of the light sections and the projection regions of the dark sections are inverted and in which the projection regions of the light sections complement each other and the projection regions of the dark sections complement each other, as shown in FIG. 5. In the first illumination image and the second illumination image in FIG. 5, the white regions indicate the projection regions of the light sections, whereas the black regions indicate the projection regions of the dark sections. Thus, the operation of the intensity-distribution changing unit 5 and the operation of the imaging element 6b are controlled by a control device (not shown) provided in the main unit 3 such that the timing at which the intensity distribution is changed by the intensity-distribution changing unit 5 and the timing at which the imaging process is performed by the imaging element 6b are synchronized with each other.

FIG. 5 illustrates image processing performed by the separation processor 7. With regard to pixels at respective positions in the first and second illumination images, an intensity value Imax when the light sections are projected and an intensity value Imin when the dark sections are projected are imaged. The separation processor 7 generates a deep-layer image (separate image) containing a large amount of information about a deep layer D of the biological tissue A from the intensity value Imin of the first and second illumination images, and generates a surface-layer image (separate image) containing a large amount of information about the surface B and a surface layer C of the biological tissue A from the intensity value Imin and the intensity value Imax of the first and second illumination images.

As shown in FIG. 6, the biological tissue A is a scattering body and includes a structure α, such as capillaries, in the surface layer C located at several tens of micrometers from the surface B, and also includes a structure β, such as thick blood vessels, in the deep layer D located deeper than the surface layer C. When illumination light L having a light-and-dark pattern is radiated onto the biological tissue A, specularly reflected (specular) light Lr, surface-scattered light Ls, and internally scattered light Ld are generated from the biological tissue A.

The specular light Lr is reflected light of the illumination light L specularly reflected at the surface B of the biological tissue A and occurs in the projection regions of the light sections.

The surface-scattered light Ls is scattered light of the illumination light L that is emitted from the surface B after entering the biological tissue A from the projection regions of the light sections and penetrating through the surface layer C while being repeatedly scattered. The surface-scattered light Ls is mostly emitted from the projection regions of the light sections.

The internally scattered light Ld is scattered light of the illumination light L that is emitted from the surface B after entering the biological tissue A from the projection regions of the light sections and penetrating through the deep layer D while being repeatedly scattered. A portion of the internally scattered light Ld is emitted from the projection regions of the light sections, whereas the remaining portion propagates to the projection regions of the dark sections so as to be emitted from the projection regions of the dark sections.

Accordingly, the intensity value Imin of the projection regions of the dark sections in the first and second illumination images is mainly based on the internally scattered light Ld and mainly includes information about the deep layer D. On the other hand, the intensity value Imax of the projection regions of the light sections in the first and second illumination images is based on the specular light Lr, the surface-scattered light Ls, and the internally scattered light Ld and includes information about the surface B, the surface layer C, and the deep layer D.

Figure 7:
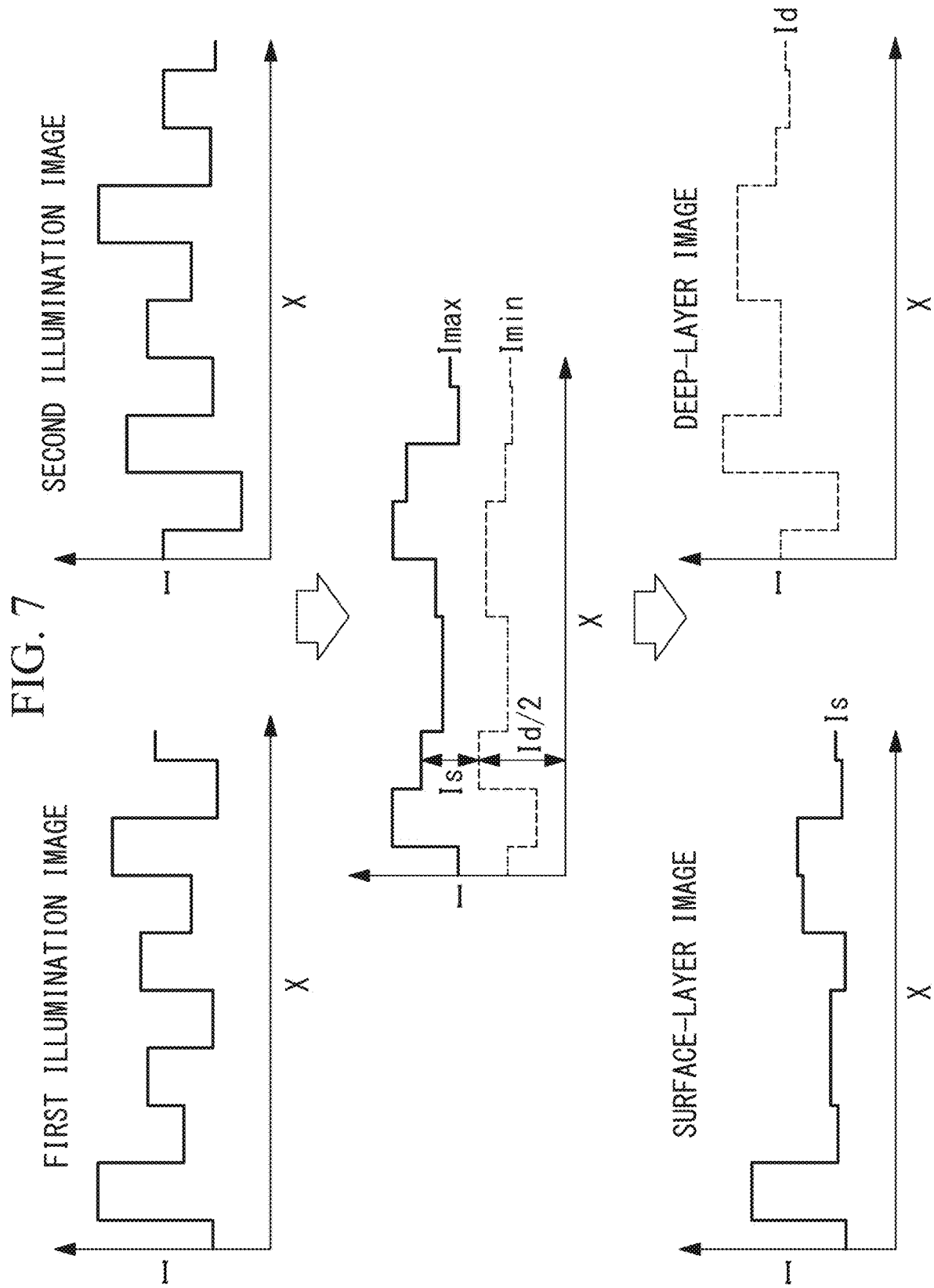
FIG. 7 illustrates a separate-image generating method in the separation processor.

FIG. 7 illustrates a specific method performed by the separation processor 7 for generating a surface-layer image and a deep-layer image. As shown in FIG. 7, the first illumination image and the second illumination image each have a brightness distribution in which the intensity values are high at pixels corresponding to the projection regions of the light sections and are low at pixels corresponding to the projection regions of the dark sections. For the sake of convenience, FIG. 7 illustrates an intensity profile where the illumination light L has a light-and-dark pattern in which the light and dark sections are repeated with a fixed period, as in the light-and-dark pattern in FIG. 2A or 2B, and the boundaries between the pixels in the image and the boundaries between the light and dark sections in the light-and-dark pattern are aligned (i.e., one light or dark section corresponds to one pixel).

As mentioned above, two intensity values Imax and Imin for each pixel are obtained from the first and second illumination images. For each pixel, the separation processor 7 sets the higher of the intensity values as the intensity value Imax and the lower of the intensity values as the intensity value Imin. Then, the separation processor 7 calculates an intensity value Is for each pixel in a surface-layer image and an intensity value Id for each pixel in a deep-layer image from the following expressions, so as to generate a surface-layer image having the intensity value Is and a deep-layer image having the intensity value Id.

$$Is = I\max - I\min$$

$$Id = I\min \times 2$$

Accordingly, a deep-layer image having the intensity value Imin mainly including information about the deep layer D is generated. By subtracting the intensity value Imin from the intensity value Imax, the information about the deep layer D is removed, so that a surface-layer image having the intensity value Is mainly including information about the surface B and the surface layer C is generated.

The surface-layer image and the deep-layer image generated by the separation processor 7 is emitted from the main unit 3 to a display device (not shown) connected to the main unit 3, and is displayed on the display device.

Such a separation processor 7 is realized as, for example, an image processing program executed by a computer. Specifically, the main unit 3 contains a central processing unit (CPU), a main storage device, such as a RAM, and an auxiliary storage device, such as a hard disk drive, and the image processing program for causing the CPU to execute the above-described processing by the separation processor 7 is stored in the auxiliary storage device. The image processing program is loaded into the main storage device from the auxiliary storage device, and the CPU executes processing in accordance with the image processing program, whereby the above-described functions of the separation processor 7 are realized.

Figure 8A:
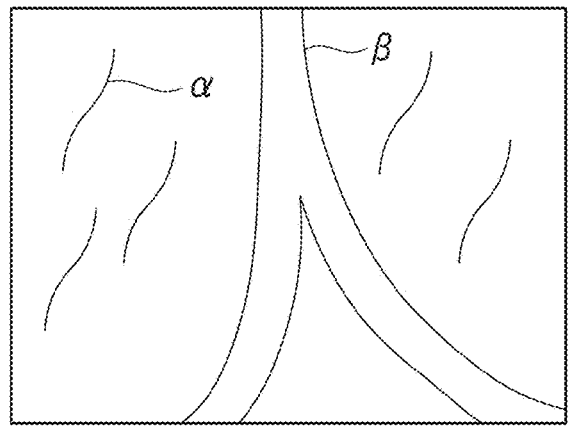
FIG. 8A illustrates an example of a normal light image of biological tissue irradiated with white light having a uniform intensity distribution.
Figure 8B:
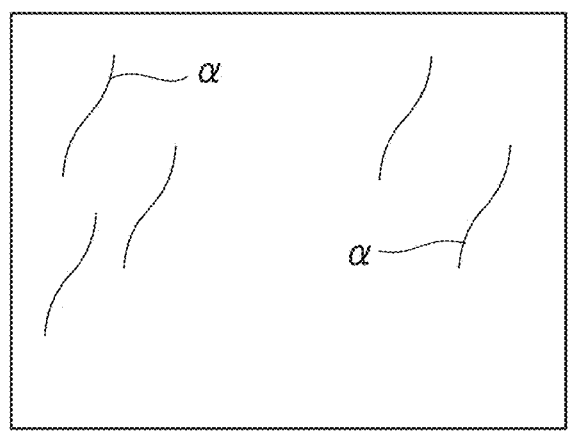
FIG. 8B illustrates an example of a surface-layer image generated by the separation processor.
Figure 8C:
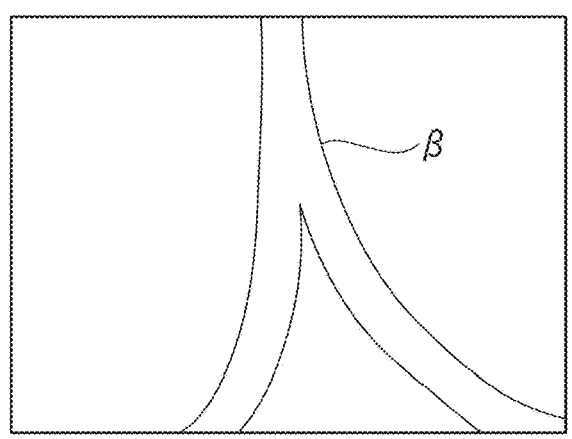
FIG. 8C illustrates an example of a deep-layer image generated by the separation processor.

FIGS. 8B and 8C illustrate examples of a surface-layer image and a deep-layer image, respectively.

When normal white light having an intensity distribution that is substantially spatially uniform is radiated onto the biological tissue A, the specular light Lr, the surface-scattered light Ls, and the internally scattered light Ld enter the imaging unit 6 in a superimposed state. Thus, as shown in FIG. 8A, in a normal light image of the biological tissue A imaged as a result of the biological tissue A being irradiated with the normal white light, a structure α, such as capillaries, in the surface layer C located at several tens of micrometers from the surface B and a structure β, such as thick blood vessels, in the deep layer D located deeper than the surface layer C are displayed together.

In contrast, according to this embodiment, the illumination light L having a light-and-dark pattern is radiated onto the biological tissue A, so that the internally scattered light Ld containing a large amount of information about the deep layer D is spatially separated from the specular light Lr and the surface-scattered light Ls containing information about the surface B and the surface layer C, thereby obtaining an illumination image in which a region where the information about the deep layer D is dominant is spatially separated from a region containing a large amount of information about the surface B and the surface layer C. Accordingly, as shown in FIGS. 8B and 8C, a surface-layer image mainly including the information about the surface B and the surface layer C and in which the image of the structure α is highlighted and a deep-layer image mainly including the information about the deep layer D and in which the image of the structure β is highlighted can be generated separately. This is advantageous in that the structure β of the deep layer D, which is especially important in endoscope observation, can be clearly observed.

The amount of information about the surface layer C and the amount of information about the deep layer D in the surface-layer image are dependent on a width Wd (see FIG. 6) of each dark section on the surface B of the biological tissue A. As the width Wd of the dark section increases, the amount of information about the deep layer D in the surface-layer image increases and the amount of information about the deep layer D in the deep-layer image decreases. In order to ensure a good balance between the amount of information about the deep layer D in the surface-layer image and the amount of information about the deep layer D in the deep-layer image, the width Wd of the dark section on the surface B of the biological tissue A is preferably 0.005 mm or more and 25 mm ore less.

If the width Wd of the dark section is smaller than 0.005 mm, the percentage of internally scattered light Ld entering the projection region of the dark section from the projection region of the light section increases, possibly causing the difference between the intensity value Imax and the intensity value Imin to decrease and resulting in a lack of information about the surface layer C included in the surface-layer image. In contrast, if the width Wd of the dark section is larger than 25 mm, the internally scattered light Ld cannot reach the center of the projection region of the dark section, possibly causing the intensity value Imin to approach zero and resulting in a lack of information about the deep layer D included in the deep-layer image.

In the light-and-dark pattern, the ratio of the area of each light section with respect to the area of each dark section (area of light section/area of dark section) preferably is more than 0.2 and less than 5. For example, in a case of a striped light-and-dark pattern, as shown in FIG. 9, the ratio of the width Wd of each dark section with respect to a width Wb of each light section preferably is 0.2 or more and 5 or less.

In order to generate a high-resolution surface-layer image and a high-resolution deep-layer image, a plurality of illumination images are required such that the intensity value Imax corresponding to when the light sections are projected and the intensity value Imin corresponding to when the dark sections are projected are obtained for all pixels. If the area of each light section and the area of each dark section significantly differ from each other, the number of required illumination images increases, or if a limited number of illumination images are to be used, the information about the surface layer C and the deep layer D required for generating a surface-layer image and a deep-layer image is insufficient, thus causing the resolution of the surface-layer image and the resolution of the deep-layer image to decrease.

By setting the ratio between the area of each light section and the area of each dark section within the above-described range, the number of illumination images required for generating a high-resolution surface-layer image and a high-resolution deep-layer image can be reduced.

As an alternative to this embodiment in which a surface-layer image and a deep-layer image are generated from two illumination images, a surface-layer image and a deep-layer image may be generated from a single illumination image, as shown in FIG. 10.

Figure 11:
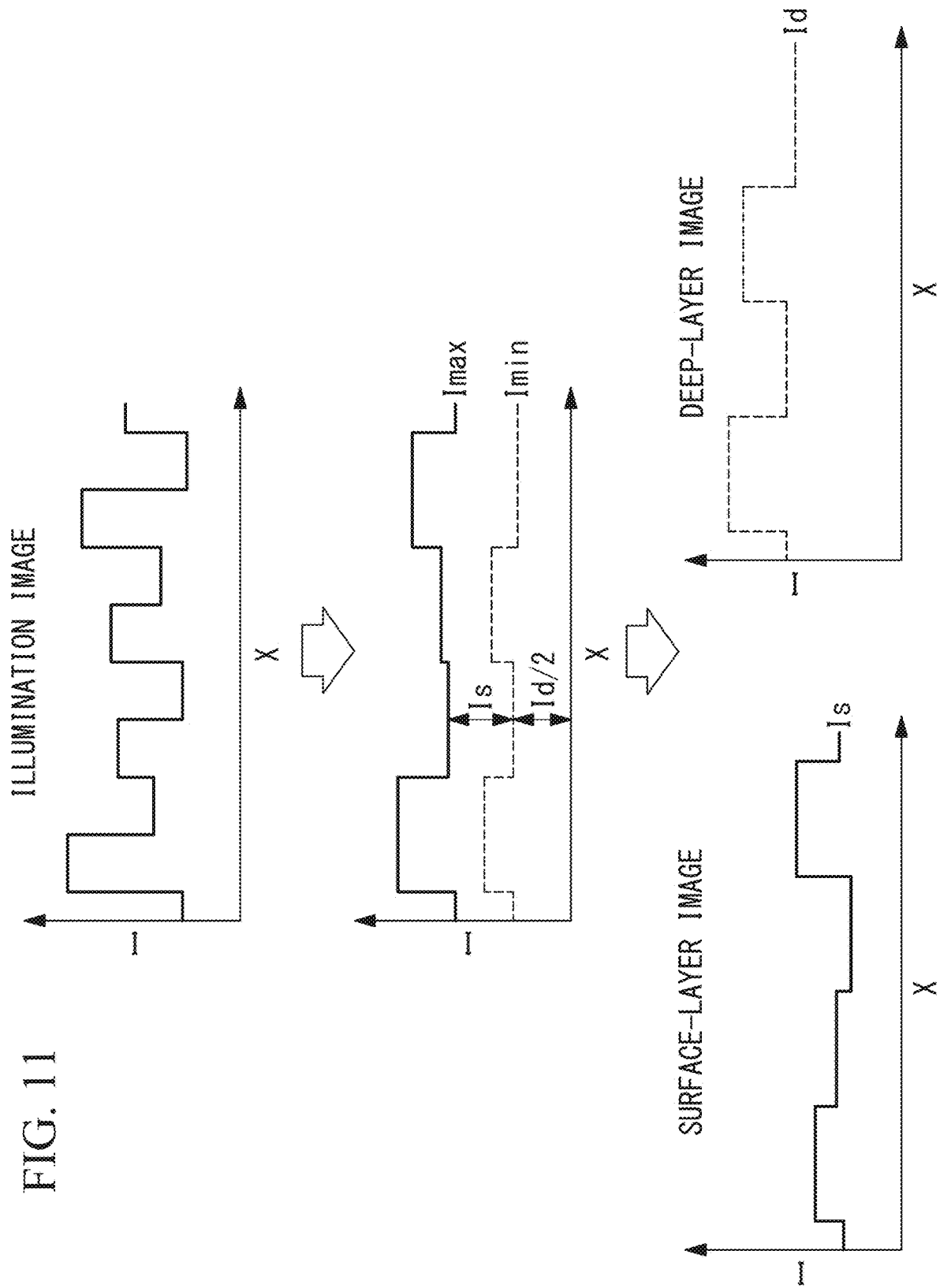
FIG. 11 illustrates a modification of the separate-image generating method in the separation processor.

In detail, as shown in FIG. 11, the projection region of one light section and the projection region of one dark section that are adjacent to each other may be treated as a single block, and the maximum intensity value and the minimum intensity value in each block may be calculated as Imax and Imin, respectively. In this case, although the resolution of the surface-layer image and the resolution of the deep-layer image decrease, a surface-layer image and a deep-layer image can be generated every time the imaging unit 6 executes an imaging process, so that the frame rates of the surface-layer image and the deep-layer image can be improved.

As an alternative to this embodiment in which the intensity-distribution changing unit 5 alternately changes the intensity distribution of the illumination light L in a discontinuous fashion between two light-and-dark patterns, in which the light sections and the dark sections are inverted, as shown in FIGS. 2A to 2F, the intensity distribution of the illumination light L may be changed continuously between two light-and-dark patterns.

Figure 12:
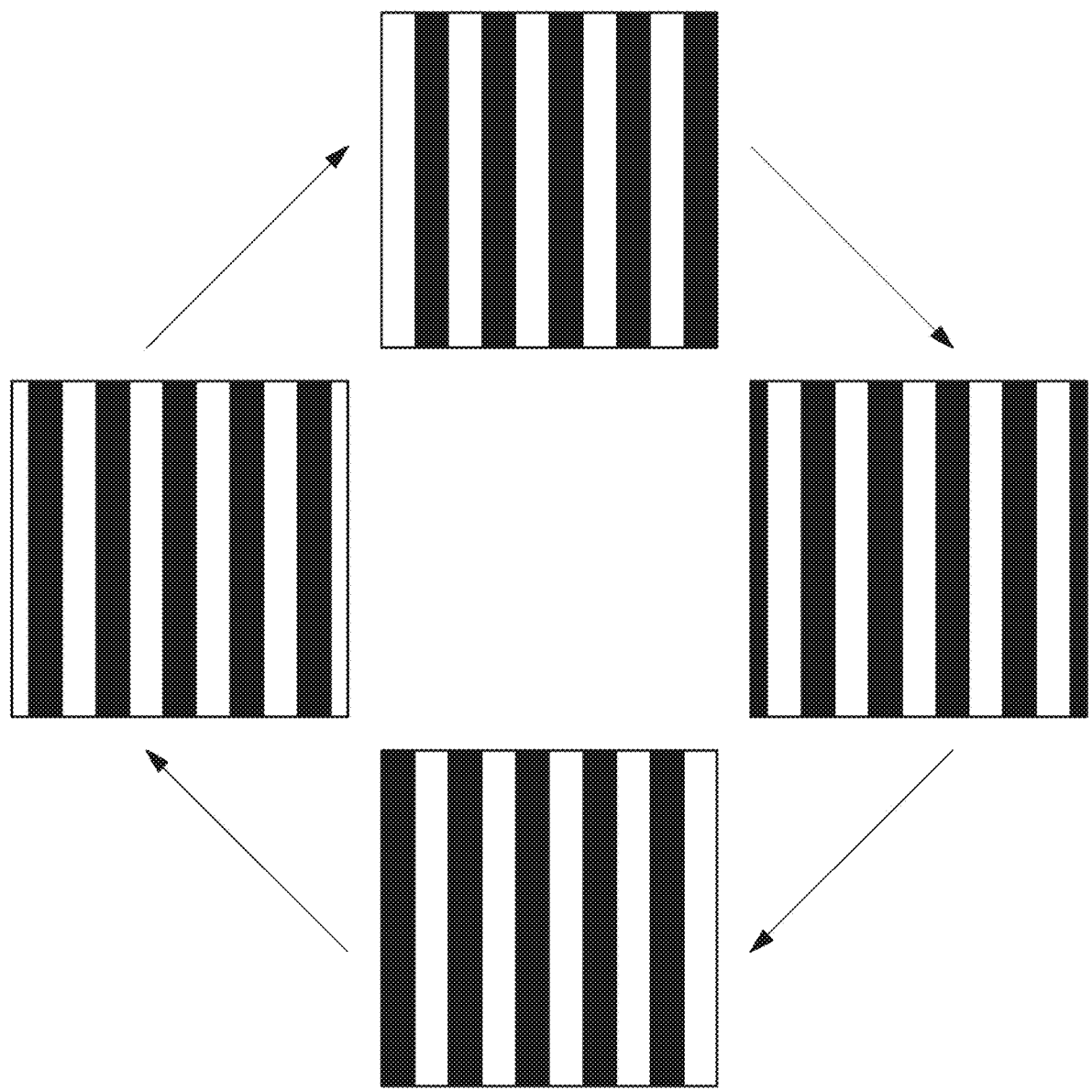
FIG. 12 illustrates another example of a temporal change of the intensity distribution of illumination light.

For example, in a case where the striped patterns in FIG. 2B are to be temporally changed by the illumination unit 41 and the intensity-distribution changing unit 51 in FIG. 4A, the light emitter 4a and the mask 4b are relatively moved in the width direction of the light sections and the dark sections, so that the light-and-dark pattern can be continuously changed, as shown in FIG. 12.

Figure 13:
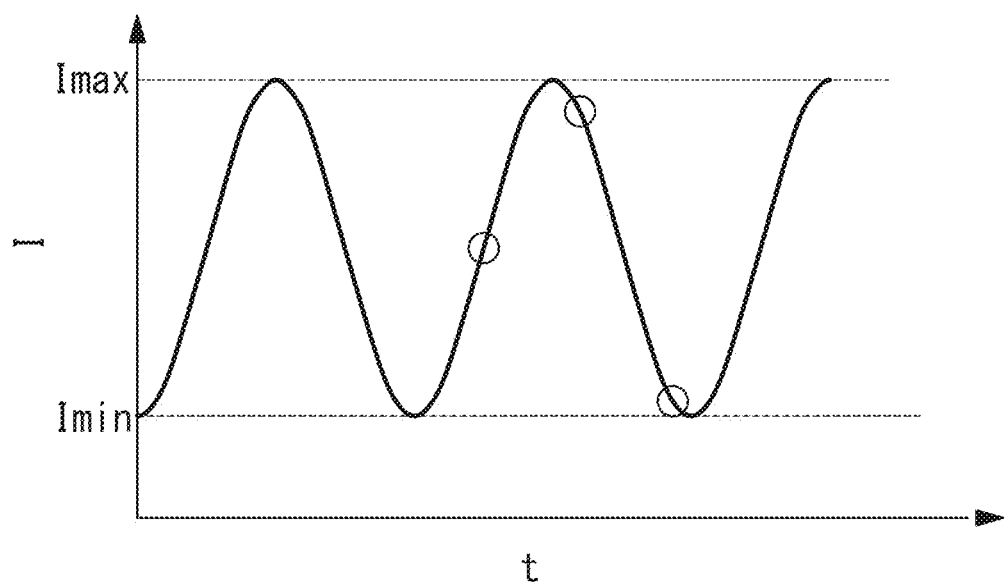
FIG. 13 illustrates a method for calculating intensity values Imax and Imin in accordance with the phase shift technique.

In the case where the light-and-dark pattern is to be continuously changed in this manner, the imaging unit 6 executes an imaging process at three or more time points at which the positions of the light sections and the positions of the dark sections are different from one another, as shown in FIG. 13, so as to images three or more illumination images in which the positions of the projection regions of the light sections and the positions the projection regions of the dark sections are different from one another. In FIG. 13, the abscissa axis indicates time t, and each circle indicates an imaging timing. The separation processor 7 may generate a surface-layer image and a deep-layer image from the three or more illumination images. In this case, since three or more intensity values are obtained with respect to the pixel at each position, the maximum intensity value and the minimum intensity value may be calculated as Imax and Imin, respectively.

If illumination light L having a sinusoidal light-and-dark pattern is to be radiated, as shown in FIG. 13, an illumination image is imaged under three or more appropriate conditions, so that Imax and Imin can be calculated for each pixel by using the phase shift technique.

In this embodiment, it is preferable that the illumination unit 4 emits a divergent beam of illumination light L toward the biological tissue A so that the light-and-dark pattern to be projected onto the surface B of the biological tissue A is expanded in proportion to the imaging distance between the biological tissue A and the imaging unit 6.

The boundary between the depth of information included in a surface-layer image and the depth of information included in a deep-layer image is dependent on the width of each dark section. The position of the boundary becomes deeper as the width of the dark section increases, so that a deep-layer image in which information at deeper positions is highlighted is obtained. Therefore, by changing the imaging distance to expand or reduce the light-and-dark pattern on the surface B of the biological tissue A, a deep-layer image in which information at different depths is highlighted can be imaged.

Figure 14A:
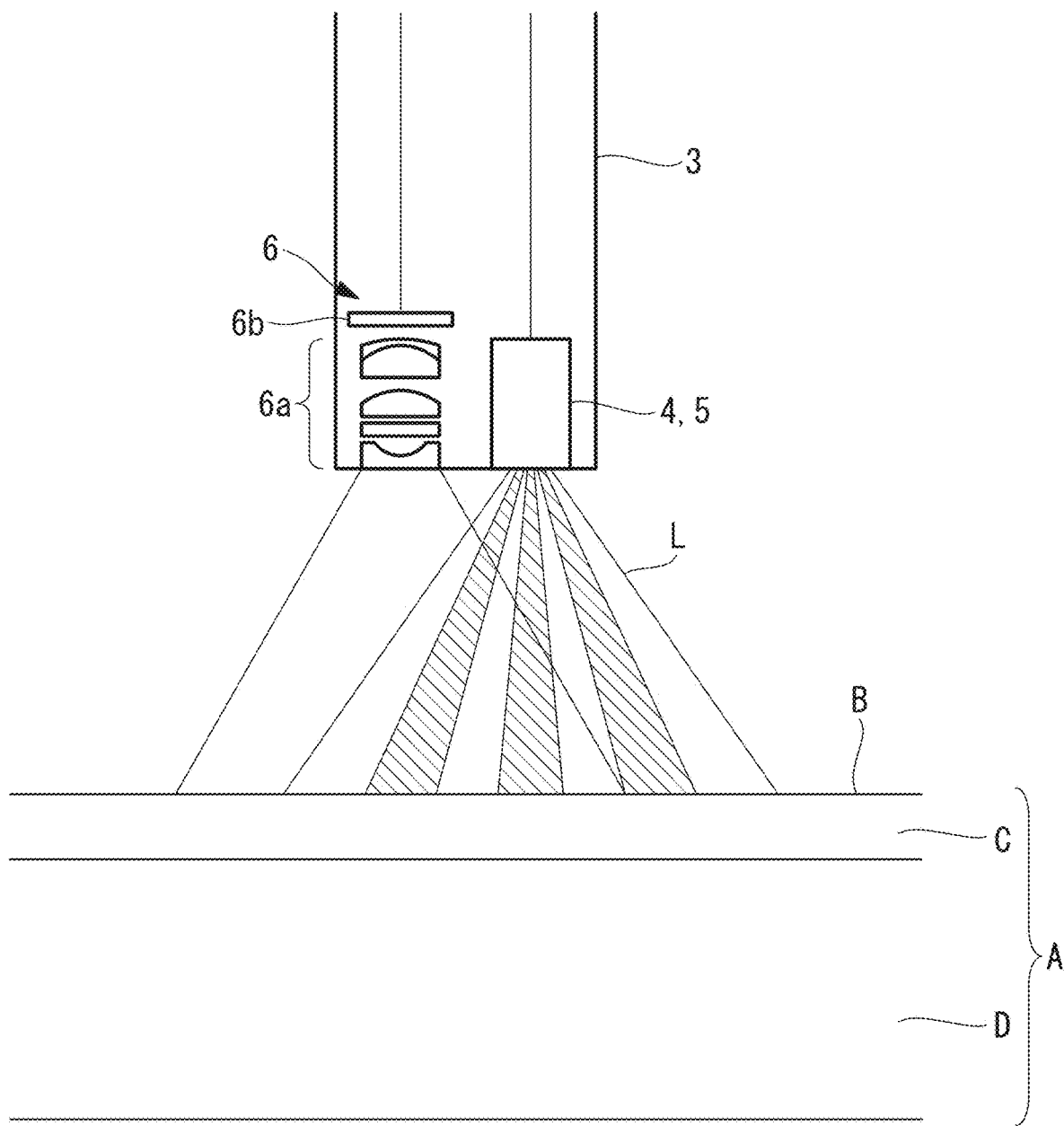
FIG. 14A illustrates the relationship between the width of each dark section and the separation depth between the surface-layer image and the deep-layer image.
Figure 14B:
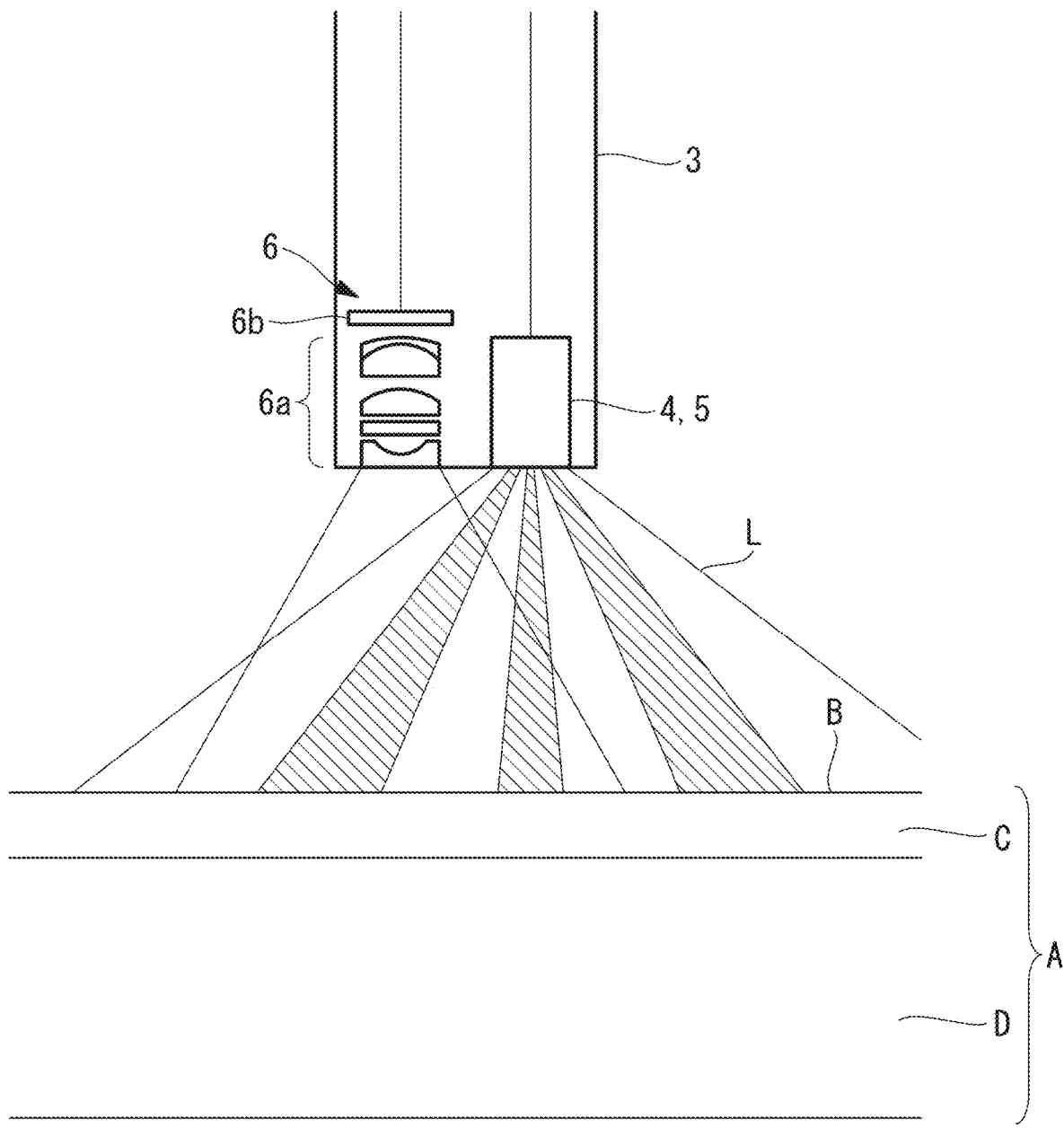
FIG. 14B illustrates the relationship between the width of each dark section and the separation depth between the surface-layer image and the deep-layer image.

FIGS. 14A and 14B qualitatively illustrate the relationship between the width of each dark section and the separation depth.

According to this embodiment, an image of the biological tissue A can be split into two images, namely, an image having information about the surface layer C and an image having information about the deep layer D. The width of each dark section of the illumination light L projected onto the surface B in FIG. 14A is smaller than the width of each dark section of the illumination light L projected onto the surface B in FIG. 14B. Although the depth of the biological tissue A that the illumination light L reaches is in the same range in both drawings, the depth of the surface layer C (i.e., the separation depth between the image having the information about the surface layer C and the image having the information about the deep layer D) is larger in FIG. 14B due to the larger width of each dark section.

The width of each dark section projected onto the surface B of the biological tissue A may be changed by expanding or reducing the overall light-and-dark pattern by changing the imaging distance mentioned above. Alternatively, an intensity-distribution adjusting unit may further be provided for changing the spatial period of the light and dark sections in the light-and-dark pattern of the illumination light L.

Figure 15:
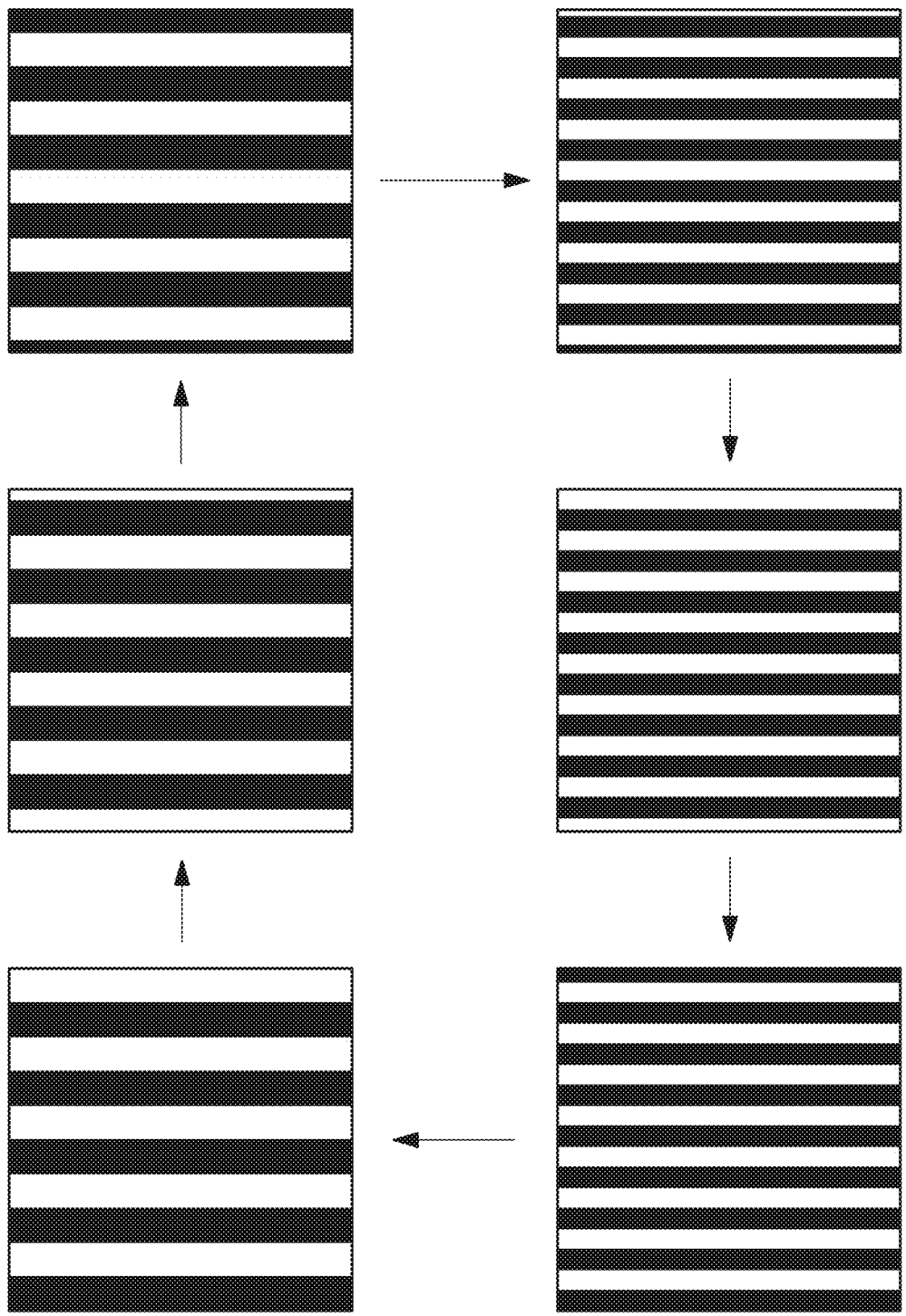
FIG. 15 illustrates another example of a temporal change of the intensity distribution of illumination light.

In a configuration equipped with an intensity-distribution adjusting unit, after a plurality of illumination images are imaged while temporally changing the light-and-dark pattern, as shown in FIG. 15, a plurality of illumination images may be imaged while temporally changing the light-and-dark pattern in which the period of the light and dark sections has been changed.

By using illumination images according to a plurality of light-and-dark patterns in which the period of the light and dark sections has been changed by the intensity-distribution adjusting unit, three or more separate images can be generated.

FIG. 16 illustrates an example of an intensity-distribution adjusting unit 8. In FIG. 16, the intensity-distribution adjusting unit 8 serves as an actuator that relatively moves the light emitter 4a and the mask 4b along the optical axis of the white light so as to change the distance between the light emitter 4a and the mask 4b. The period of the light sections and the dark sections projected onto the surface B of the biological tissue A becomes smaller with increasing distance between the light emitter 4a and the mask 4b.

Alternatively, the intensity-distribution adjusting unit used may be a zoom lens that is constituted by a plurality of lenses at least one of which is movable along the optical axis. As another alternative, if the illumination unit 42 equipped with the mask 4e formed of a liquid crystal element is used, the intensity-distribution adjusting unit may change the period of the light sections and the dark sections by electrically controlling the mask 4e.

In this embodiment, an imaging-distance measuring unit that measures the imaging distance between the biological tissue A and the imaging unit 6 may further be provided. The intensity-distribution adjusting unit may adjust the spatial period of the light sections and the dark sections in the light-and-dark pattern based on the imaging distance such that the spatial period of the light sections and the dark sections projected onto the surface B of the biological tissue A is maintained constant without being dependent on the imaging distance.

Accordingly, a deep-layer image containing information at a predetermined depth can be generated without being dependent on the imaging distance.

The imaging-distance measuring unit used may be any known means that can measure the imaging distance without coming into contact with the biological tissue A. If the light-and-dark pattern is a linear striped pattern in which the intensity changes in a sinusoidal pattern, as shown in FIGS. 2B and 3B, the imaging-distance measuring unit may use the phase shift technique to calculate the imaging distance from an illumination image imaged by the imaging unit 6.

Figure 17:
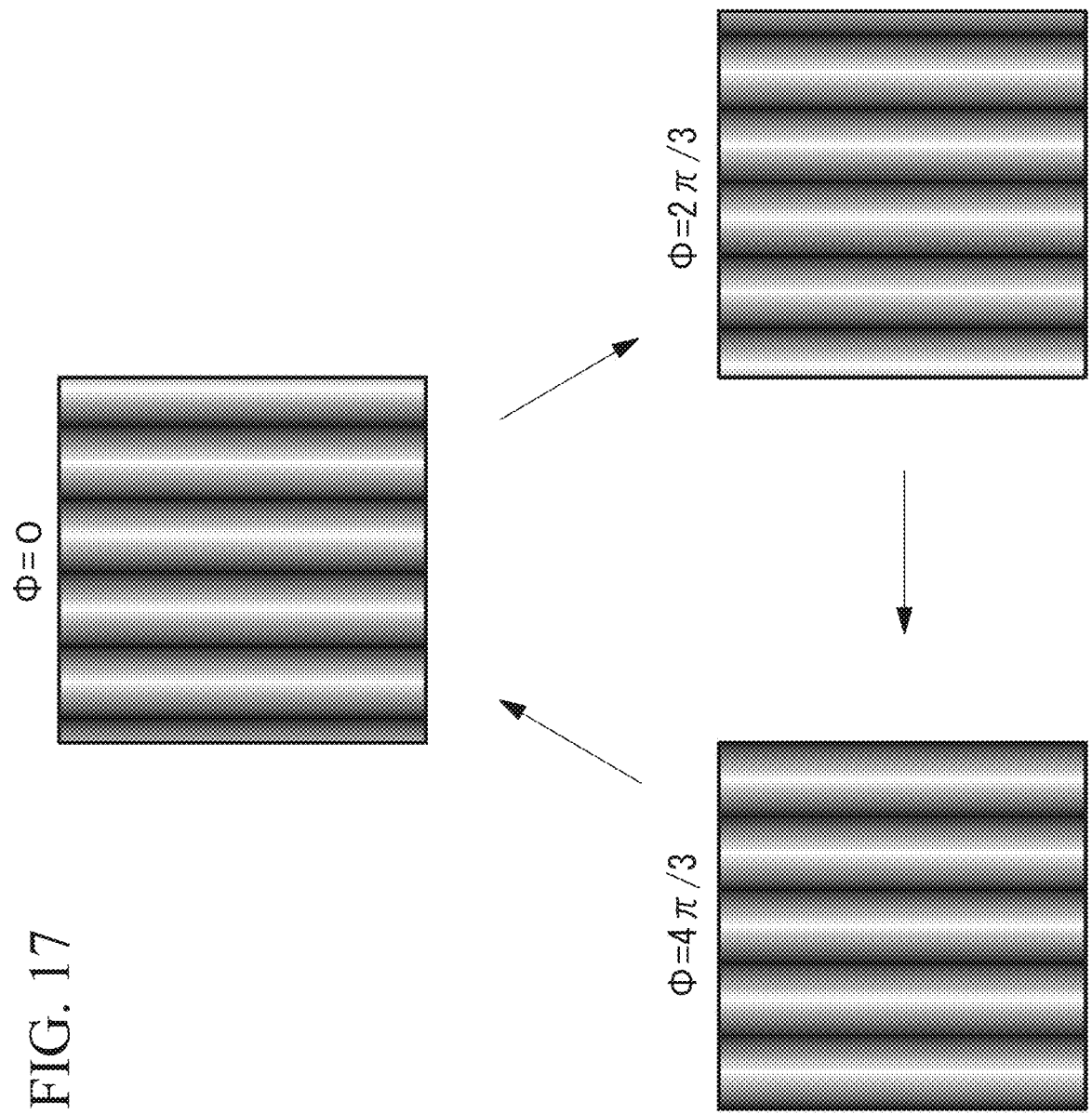
FIG. 17 illustrates a method for calculating the intensity values Imax and Imin in accordance with the phase shift technique.

In this embodiment, the intensity values used in the two illumination images are the intensity values Imax and Imin. Alternatively, if the light-and-dark pattern is a linear striped pattern in which the intensity changes in a sinusoidal pattern, as shown in FIGS. 2B and 3B, the intensity values Imax and Imin for each pixel may be calculated in accordance with the phase shift technique. As shown in FIG. 17, according to the phase shift technique, the maximum intensity value Imax and the minimum intensity value Imin for each pixel can be obtained from three illumination images having different phases $\Phi$ of light-and-dark patterns. Therefore, a surface-layer image and a deep-layer image having resolutions equal to that of the illumination images can be generated from a small number of illumination images.

Although the illumination unit 4 emits white illumination light L in this embodiment, the illumination light L is not limited to white light and may alternatively be light having other wavelength characteristics. For example, the illumination light L may be infrared light or may be red, green, or blue monochromatic light. Alternatively, the illumination light L may be constituted by a plurality of light beams having different wavelengths, such as white light constituted by a mixture of three light beams, namely, red, green, and blue light beams.

Figure 18:
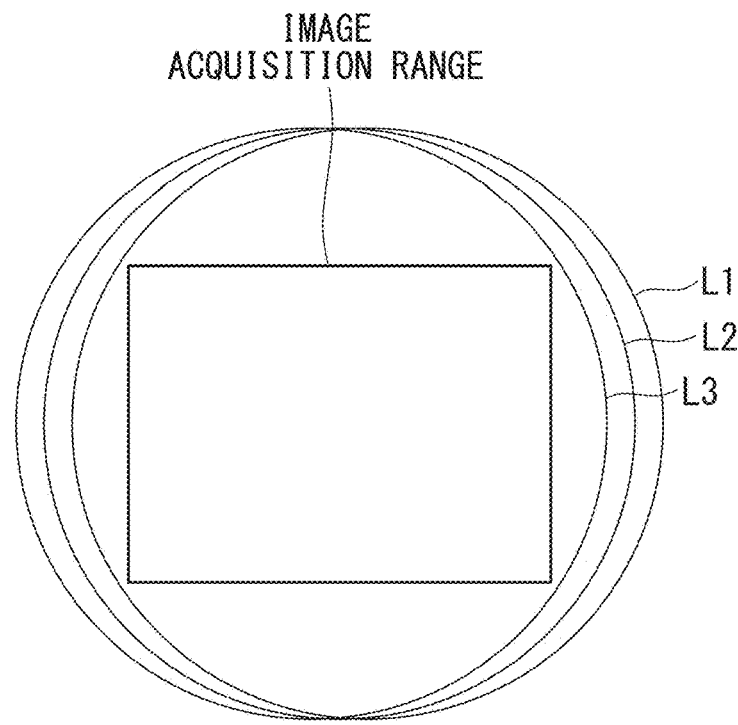
FIG. 18 illustrates the positional relationship between irradiation ranges of a plurality of light beams that constitute illumination light.

If the illumination light L is constituted by a plurality of light beams L1, L2, and L3, the irradiation ranges of the plurality of light beams L1, L2, and L3 on the surface B of the biological tissue A do not have to be completely aligned with one another, as shown in FIG. 18, and may be misaligned with one another within a range such that all of the irradiation ranges of the light beams L1, L2, and L3 overlap one another in the imaging range of the imaging unit 6.

If the plurality of light beams having different wavelengths are to be used as the illumination light L, the intensity distribution of each light beam may be varied in accordance with the wavelength such that the period of the light sections and the dark sections becomes smaller with increasing wavelength.

Figure 19:
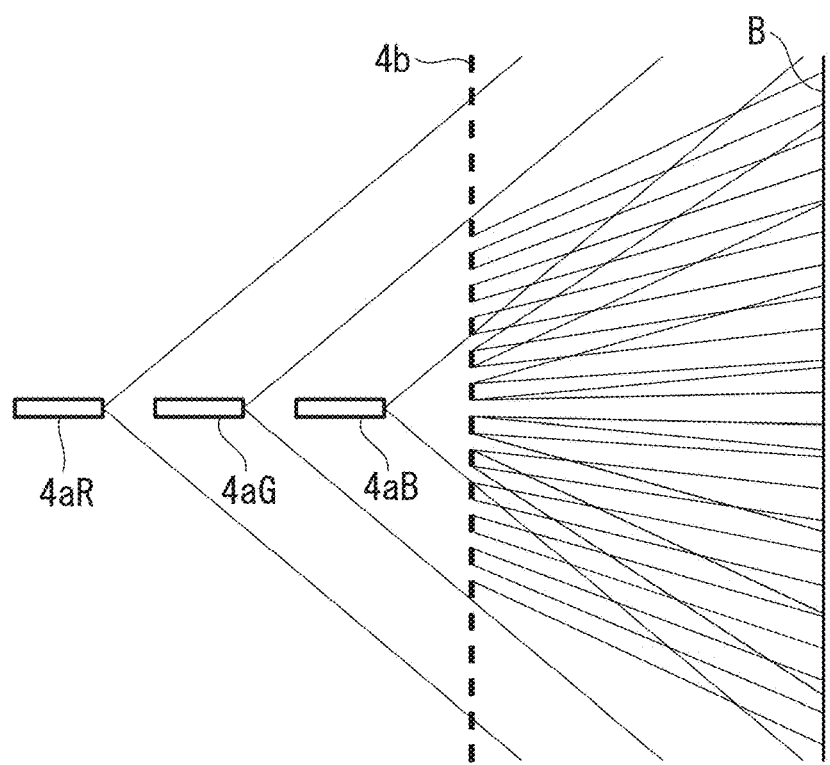
FIG. 19 illustrates the configuration of a modification of the illumination unit.

For example, as shown in FIG. 19, if three light emitters 4aR, 4aG, and 4aB that respectively emit red (R), green (G), and blue (B) light beams are used, the distance between each of the light emitters 4aR, 4aG, and 4aB and the mask 4b is set such that the distance from the mask 4b increases with increasing wavelength.

Normally, light is scattered more intensely by a scattering body as the wavelength decreases. Therefore, the B light beam is less likely to reach the deep layer D of the biological tissue A, as compared with the R light beam, and information included in the internally scattered light Ld of the B light beam is information about a shallower position, as compared with the internally scattered light Ld of the R light beam. By making the period of the light sections and the dark sections smaller with increasing wavelength, the depth of the information included in each light beam can be controlled such that the internally scattered light Ld of any of the R, G, and B light beams has information at the same depth.

Figure 20A:
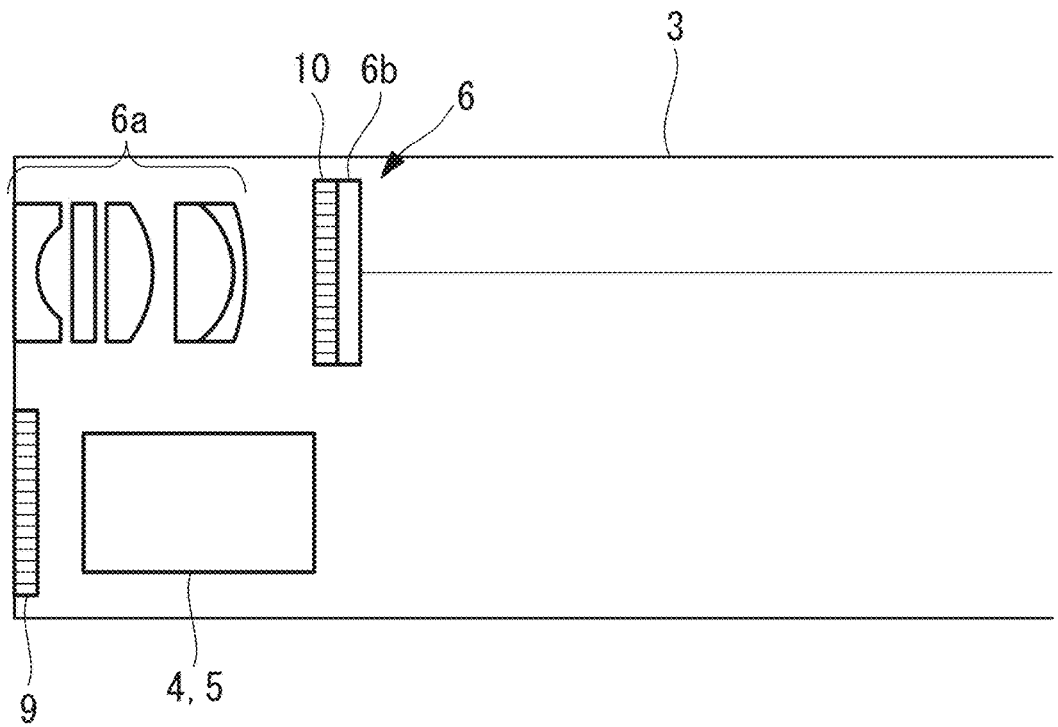
FIG. 20A is a partial configuration diagram illustrating a modification of the endoscope system equipped with a polarization controller and a polarization selector.

In this embodiment, the information about the biological tissue A is separated into two pieces of information, namely, the information about the surface B and the surface layer C and the information about the deep layer D. Alternatively, as shown in FIGS. 20A and 20B, the information about the surface B and the information about the surface layer C may be further separated by utilizing polarization.

A light polarizer (polarization controller) 9 that controls the polarization state of illumination light emitted from the illumination unit 4 is provided at the distal end of the endoscope 2, and a light polarizer (polarization selector) 10 that selects the polarization state of light entering the imaging unit 6 from the biological tissue A is provided in front of the imaging unit 6. By aligning the polarization direction of the light polarizer 10 with the polarization direction of the light polarizer 9, an illumination image that includes the surface-scattered light Ls and the specular light Lr can be imaged. By setting the polarization direction of the light polarizer 10 orthogonal to the polarization direction of the light polarizer 9, an illumination image that includes the surface-scattered light Ls but does not include the specular light Lr can be imaged.

Figure 20B:
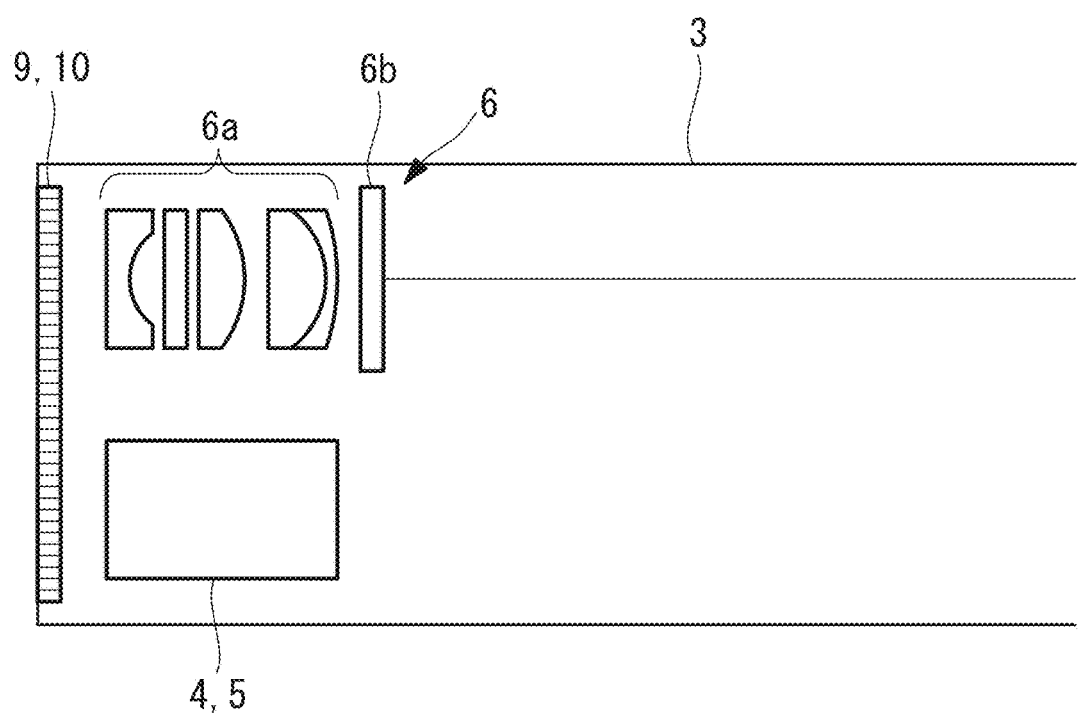
FIG. 20B is a partial configuration diagram illustrating another modification of the endoscope system equipped with the polarization controller and the polarization selector.

As shown in FIG. 20B, the light polarizer 10 is disposed at the distal end of the endoscope 2, so that the light polarizer 9 for the illumination unit 4 and the light polarizer 10 for the imaging unit 6 can be used as a shared component.

In this embodiment, an image combining unit that generates a combined image by combining a surface-layer image and a deep-layer image may further be provided. For example, similar to the separation processor 7, the image combining unit is realized as an image processing program stored in the auxiliary storage device in the main unit 3 and executed by the CPU.

The image combining unit is capable of arbitrarily changing the combination ratio P and the combination ratio Q of the surface-layer image and the deep-layer image, and changes the combination ratio P and the combination ratio Q so as to generate a combined image in which one of the information about the surface layer C and the information about the deep layer D is highlighted while both are maintained.

In detail, as shown in FIG. 21, the surface-layer image and the deep-layer image are combined in a ratio of 1:1, so that a combined image equivalent to a normal light image is obtained. On the other hand, by increasing the combination ratio P of the surface-layer image, a combined image in which the information about the surface layer C is highlighted is obtained. By increasing the combination ratio Q of the deep-layer image, a combined image in which the information about the deep layer D is highlighted is obtained. For example, the combination ratio P and the combination ratio Q are set by a user via input means (not shown) connected to the main unit 3.

The combination ratio P and the combination ratio Q of the surface-layer image and the deep-layer image may be settable for each pixel. An intensity value $I_{ij}$ of each pixel ij of a combined image can be calculated from the expression indicated below. In this case, ij (i=1, 2, ..., n, j=1, 2, ..., m) indicates positional coordinates of a pixel in an n-pixel by m-pixel image. In the expression indicated below, $P_{ij}$ indicates a combination ratio of a pixel ij in the surface-layer image, and $Q_{ij}$ indicates a combination ratio of a pixel ij in the deep-layer image.

$$I_{ij} = P_{ij} * I_{sij}/(I_{sij}+I_{dij}) + Q_{ij} * I_{dij}/(I_{sij}+I_{dij})$$

For example, the user may set the combination ratio $P_{ij}$ and the combination ratio $Q_{ij}$ while observing the surface-layer image and the deep-layer image displayed on the display device.

As a result, the following aspect is read from the above described embodiment of the present invention.

An aspect of the present invention provides an endoscope system including: an illumination unit that radiates illumination light onto a subject, the illumination light having a spatially non-uniform intensity distribution including a light section and a dark section in a beam cross section orthogonal to an optical axis; an imaging unit that images an illumination image of the subject irradiated with the illumination light; and a separation processor that generates two separate images from the illumination image imaged by the imaging unit. One of the two separate images is a deep-layer image including a larger amount of information about a deep-layer region of the subject than the other one of the two separate images. Among intensity values of pixels within the illumination image respectively corresponding to the light section, the dark section, and a section having intermediate intensity between the light section and the dark section in the intensity distribution, the separation processor generates the two separate images based on at least two of the intensity values.

According to the aspect of the present invention, when the illumination light is radiated onto the subject serving as a scattering body, specularly reflected (specular) light specularly reflected at the surface of the subject, surface-scattered light emitted from the surface of the subject after being scattered in a surface layer inside the subject, and internally scattered light emitted from the surface of the subject after being scattered in a deep layer inside the subject occur. By radiating the illumination light having the spatially non-uniform intensity distribution onto the subject from the illumination unit, the internally scattered light is spatially separated from the specular light and the surface-scattered light. In other words, the specular light, the surface-scattered light, and the internally scattered light occur in the light section, whereas the internally scattered light entering the dark section from the light section dominantly occurs in the dark section.

Therefore, the region corresponding to the dark section in the illumination image imaged by the imaging unit includes a large amount of information about the deep layer, whereas the region corresponding to the light section includes a large amount of information about the surface and the surface layer. The term "information" refers to, for example, the amount of light emitted from biological tissue after entering the biological tissue and undergoing modulation, such as scattering and absorption, by the biological tissue and internal structures therein. Among the intensity values of the pixels respectively corresponding to the light section, the dark section, and the section having intermediate intensity between the light section and the dark section, the separation processor generates the two separate images, including a large amount of information at different depths, based on at least two of the intensity values.

In detail, the separation processor can generate a separate image (deep-layer image) including a large amount of information about the deep layer of the subject on the basis of the intensity value of the pixels in the region corresponding to the dark section. Moreover, the separation processor can generate a separate image (surface-layer image) including a large amount of information about the surface and the surface layer of the subject based on the intensity value of the pixels in the region corresponding to the light section. Furthermore, based on the intensity value of the pixels in the region corresponding to the section having the intermediate intensity value between the light section and the dark section, the separation processor can generate a separate image including a large amount of information about a position shallower than the deep layer but deeper than the surface layer.

In the above aspect, the endoscope system may further include an intensity-distribution changing unit that temporally changes the intensity distribution of the illumination light such that the light section and the dark section are positionally interchanged. The illumination image imaged by the imaging unit may include at least two illumination images of the subject irradiated with beams of the illumination light in which the intensity distribution is different between the beams. The separation processor may generate the two separate images from the at least two illumination images.

By temporally changing the intensity distribution of the illumination light and interchanging the positions of the light section and the dark section to be projected onto the subject, an intensity value corresponding to when the light section to be used for generating a surface-layer image is projected and an intensity value corresponding to when the dark section to be used for generating a deep-layer image is projected can be imaged for each pixel, so that a high-resolution surface-layer image and a high-resolution deep-layer image can be generated.

In the above aspect, the light section and the dark section may be spatially repeated in the intensity distribution of the illumination light.

The light section and the dark section are alternately repeated in this manner so that the internally scattered light can be separated evenly within the imaging range, whereby the separate images can be effectively generated.

In the above aspect, the intensity distribution may have a striped pattern in which the light section and dark section are alternately repeated in a width direction to form a stripe shape.

Accordingly, the internally scattered light can be effectively separated using a simple light-and-dark pattern. Moreover, in order to interchange the positions of the striped light and dark sections in the intensity distribution, the light and dark sections in the intensity distribution may simply be moved in the width direction of the stripes, so that the intensity distribution of the illumination light can be easily temporally changed.

In the above aspect, an intensity profile, in the width direction, of the light section and the dark section in the intensity distribution of the illumination light may have a substantially sinusoidal shape.

By radiating illumination light whose intensity spatially changes in a sinusoidal pattern onto the subject in this manner, a surface-layer-image intensity value corresponding to when light of the highest intensity is radiated and a deep-layer-image intensity value corresponding to when light is not radiated can be calculated using the phase shift technique, so that good high-resolution separate images can be generated even from a small number of illumination images.

In the above aspect, a width of a part where the dark section is projected onto a surface of the subject may be 0.005 mm or more and 25 mm or less.

Accordingly, internally scattered light can be spatially separated from specular light and surface-scattered light with high accuracy, so that a good deep-layer image and a good surface-layer image can be generated. If the width of the dark section projected onto the surface of the subject is smaller than 0.005 mm, the amount of information about the surface layer included in the deep-layer image increases, and the deep-layer image becomes closer to a normal light image of the subject irradiated with substantially spatially uniform light. If the width of the dark section projected onto the surface of the subject is larger than 25 mm, the amount of information about the deep layer included in the deep-layer image becomes insufficient, thus making it difficult to generate a clear deep-layer image.

In the above aspect, the endoscope system may include an intensity-distribution adjusting unit that changes a period of the light section and the dark section in the intensity distribution.

The boundary between the depth of information included in the surface-layer image that includes a large amount of information about the surface layer and the depth of information included in the deep-layer image that includes a large amount of information about the deep layer is dependent on the width of the dark section on the subject. By using the intensity-distribution adjusting unit to adjust the width of the dark section on the subject, the depth of the boundary can be controlled such that a deep-layer image in which information at a desired depth is highlighted can be generated.

In the above aspect, the separation processor may generate three or more separate images based on two or more illumination images imaged by radiating two or more illumination light beams having different widths in the dark section.

Accordingly, by using a plurality of illumination images of the subject irradiated with illumination light beams having different widths in the dark section, three or more separate images including a large amount of information at different depths can be generated.

In the above aspect, the endoscope system may further include an imaging-distance measuring unit that measures an imaging distance between the imaging unit and the subject. The intensity-distribution adjusting unit may change a period of the light section and the dark section in the intensity distribution based on the imaging distance such that the intensity distribution of the illumination light on the subject is fixed regardless of the distance between the imaging unit and the subject.

Accordingly, a deep-layer image including information at a fixed depth can be generated without being dependent on the imaging distance.

In the above aspect, the illumination unit may emit the illumination light as a divergent beam so that a pattern of the light section and the dark section on the subject is expanded in proportion to an imaging distance between the imaging unit and the subject.

Accordingly, by simply changing the imaging distance, the period of the light section and the dark section on the subject can be changed, so that a deep-layer image including information at different depths can be obtained.

In the above aspect, the illumination light may include a plurality of light beams having different wavelengths. The plurality of light beams may each have the intensity distribution in which a period of the light section and the dark section becomes smaller with increasing wavelength.

The light entering the subject reaches a deeper position as the wavelength increases, so that internally scattered light of light having a longer wavelength includes information about a deeper position. By making the period of the light section and the dark section smaller with increasing wavelength, a difference in depths of information caused by a difference in wavelengths can be reduced.

In the above aspect, in the intensity distribution of the illumination light, a ratio of an area of the light section with respect to an area of the dark section may be 0.2 or more and 5.0 or less.

In order to generate a good high-resolution surface-layer image and a good high-resolution deep-layer image, it is preferable that two intensity values corresponding to when the light section and the dark section are projected be obtained for each pixel. If the difference between the area of the light section and the area of the dark section increases, a larger number of illumination images need to be imaged to obtain the two intensity values for each pixel. By setting the ratio between the area of the light section and the area of the dark section within the aforementioned range, a good surface-layer image and a good deep-layer image can be generated using a small number of illumination images.

In the above aspect, the endoscope system may further include a polarization controller that controls a polarization state of the illumination light and a polarization selector that selects a polarization state of light entering the imaging unit from the subject.

Specular light has the same polarization state as the illumination light, whereas surface-scattered light and internally scattered light do not have specific polarization states. Therefore, by adjusting the polarization state of the light entering the imaging unit relative to the polarization state of the illumination light, the entering and blocking of the specular light into and from the imaging unit can be selectively controlled, so that the specular light and the surface-scattered light can be separated from each other.

In the above aspect, the endoscope system may further include an image combining unit that combines the two separate images. The image combining unit may be capable of changing combination ratios of the two separate images to be combined.

Accordingly, a combined image in which one of the information about the surface layer and the information about the deep layer is highlighted can be generated while the information about the surface layer and the information about the deep layer are maintained.

REFERENCE SIGNS LIST 1 endoscope system
2 endoscope
3 main unit
4, 41, 42, 43 illumination unit
5, 51, 52, 53, 54 intensity-distribution changing unit
6 imaging unit
7 separation processor
8 intensity-distribution adjusting unit
9 light polarizer (polarization controller)
10 light polarizer (polarization selector)
L illumination light
A biological tissue
B surface
C surface layer
D deep layer

The invention claimed is:

1. An endoscope system comprising:
an illumination unit is configured to radiate illumination light onto a subject, the illumination light having a spatially non-uniform intensity distribution including a light section and a dark section in a beam cross section orthogonal to an optical axis;
an imaging unit configured to image at least two illumination images of the subject irradiated with the illumination light;
a processor configured to generate two separate images from the at least two illumination images imaged by the imaging unit; and
an intensity-distribution changing unit configured to temporally change the intensity distribution of the illumination light such that the light section and the dark section are positionally interchanged,
wherein the at least two illumination images are imaged by the imaging unit by irradiating the subject with the illuminated light in which the intensity distribution is different between the beams, and intensity values of corresponding pixels within respective illumination images of the at least two illumination images are mutually different, and
wherein one of the two separate images is a deep-layer image including a larger amount of information about a deep-layer region of the subject than the other one of the two separate images, and the other one of the two separate images is a surface-layer image including a larger amount of information about a surface and a surface-layer region of the subject than the deep-layer image, and
wherein, the processor generates the two separate images based on the intensity values of each pixel of the at least two illumination images.

2. The endoscope system according to claim 1, wherein the light section and the dark section are spatially repeated in the intensity distribution of the illumination light.

3. The endoscope system according to claim 2, wherein the intensity distribution has a striped pattern in which the light section and dark section are alternately repeated in a width direction to form a stripe shape.

4. The endoscope system according to claim 3, wherein an intensity profile, in the width direction, of the light section and the dark section in the intensity distribution of the illumination light has a substantially sinusoidal shape.

5. The endoscope system according to claim 2, wherein a width of a part where the dark section is projected onto a surface of the subject is 0.005 mm or more and 25 mm or less.

6. The endoscope system according to claim 1, further comprising:
an intensity-distribution adjusting unit that is configured to change a period of the light section and the dark section in the intensity distribution.

7. The endoscope system according to claim 6, further comprising:
an imaging-distance measuring unit that is configured to measure an imaging distance between the imaging unit and the subject,
wherein the intensity-distribution adjusting unit changes a period of the light section and the dark section in the intensity distribution based on the imaging distance such that the intensity distribution of the illumination light on the subject is fixed regardless of the distance between the imaging unit and the subject.

8. The endoscope system according to claim 1, wherein the processor generates three or more separate images based on the at least two illumination images imaged by radiating two or more illumination light beams having different widths in the dark section.

9. The endoscope system according to claim 1, wherein the illumination unit emits the illumination light as a divergent beam so that a pattern of the light section and the dark section on the subject is expanded in proportion to an imaging distance between the imaging unit and the subject.

10. The endoscope system according to claim 1,
wherein the illumination light comprises a plurality of light beams having different wavelengths, and
wherein the plurality of light beams each have the intensity distribution in which a period of the light section and the dark section becomes smaller with increasing wavelength.

11. The endoscope system according to claim 1, wherein, in the intensity distribution of the illumination light, a ratio of an area of the dark section with respect to an area of the light section is 0.2 or more and 5.0 or less.

12. The endoscope system according to claim 1, further comprising:
a polarization controller that is configured to control a polarization state of the illumination light; and
a polarization selector that is configured to select a polarization state of light entering the imaging unit from the subject.

13. The endoscope system according to claim 1, wherein the processor being further configured to:
combine the two separate images, and
change combination ratios of the two separate images to be combined.

14. The endoscope system according to claim 1,
wherein, the processor is configured to generate the two separate images based on an intensity value Imax of each pixels of the illumination images when the light sections of the at least two illumination images are projected and an intensity value Imin of each of the pixels of the illumination images when the dark sections of the at least two illumination images are projected.

15. The endoscope system according to claim 14,
wherein the intensity value Imin is based on an internally scattered light of the subject and includes information about the deep layer region of the subject,
the intensity value Imax is based on a specular light, a surface-scattered light, and the internally scattered light of the subject and includes information about the surface, the surface layer, and the deep layer,
wherein the processor is configured to calculate an intensity value Is for each pixel in a surface-layer image and an intensity value Id for each pixel in a deep-layer image from the following expressions, and generates the two separate images;

$Is = I\max - I\min$ $Id = I\min \times 2.$

16. The endoscope system according to claim 1,
wherein the intensity distribution of the illumination light has a spatial sinusoidal light-and-dark pattern,
wherein the imaging unit images three or more illumination images in which phases of the spatial sinusoidal light-and-dark pattern are mutually different each other, and
wherein from the three or more illumination images, the processor is configured to generate at least the two separation images by using a phase shift technique.

* * * * *